(12) United States Patent  (10) Patent No.: US 8,531,781 B2
Orihara et al.  (45) Date of Patent: Sep. 10, 2013

(54) OBJECTIVE OPTICAL SYSTEM

(75) Inventors: Tatsuya Orihara, Hachioji (JP);
Tsutomu Uzawa, Hidaka (JP)

(73) Assignee: Olympus Medical Systems Corp.,
Tokyo (JP)

( * ) Notice: Subject to any disclaimer, the term of this patent is extended or adjusted under 35 U.S.C. 154(b) by 105 days.

(21) Appl. No.: 13/066,809

(22) Filed: Apr. 25, 2011

(65) Prior Publication Data

US 2011/0286112 A1  Nov. 24, 2011

Related U.S. Application Data

(63) Continuation of application No. PCT/JP2010/062058, filed on Jul. 16, 2010.

(30) Foreign Application Priority Data

Sep. 1, 2009 (JP) .................................. 2009-201824

(51) Int. Cl.
*G02B 13/18* (2006.01)

(52) U.S. Cl.
USPC .......................................................... 359/716

(58) Field of Classification Search
USPC ................. 359/708, 716; D16/134, 210, 218
See application file for complete search history.

(56) References Cited

U.S. PATENT DOCUMENTS

| | | | |
|---|---|---|---|
| 4,916,534 A | | 4/1990 | Takhashi et al. |
| 5,223,982 A | | 6/1993 | Suzuki et al. |
| 5,418,649 A | * | 5/1995 | Igarashi ........................ 359/716 |
| 5,436,767 A | * | 7/1995 | Suzuki et al. ................. 359/716 |
| 5,978,158 A | * | 11/1999 | Nagata .......................... 359/753 |
| 6,256,155 B1 | | 7/2001 | Nagaoka |
| 6,547,722 B1 | * | 4/2003 | Higuma et al. ............... 600/133 |

(Continued)

FOREIGN PATENT DOCUMENTS

| | | |
|---|---|---|
| EP | 1 526 398 | 4/2005 |
| EP | 1 903 369 | 3/2008 |

(Continued)

OTHER PUBLICATIONS

European Office Action, dated Apr. 18, 2013, issued in corresponding European Patent Application No. 10813573.2.

(Continued)

*Primary Examiner* — Alessandro Amari
*Assistant Examiner* — Jie Lei
(74) *Attorney, Agent, or Firm* — Kenyon & Kenyon LLP

(57) ABSTRACT

An objective optical system includes, in order from an object, a negative-powered first-lens, an aperture stop, a positive-powered second-lens, and a third-lens, wherein: a surface of the first-lens which is closest to an image is a concave surface; a surface of the second-lens which is closest to the image is an aspheric surface; a surface of the third-lens which is closest to the object is a convex surface; the objective optical system has a three-group, three-lens configuration in which each of the first- to third-lenses is made up of a single lens and all surfaces of the three lenses have power; a distance d_L23 between the second-lens and the third-lens is smaller than a distance d_L12 between the first-lens and the second-lens, satisfying a conditional d_L23/d_L12<0.25; and a focal length f_L2 of the second-lens, and a focal length f_L3 of the third-lens satisfy the conditional 1.7<f_L3/f_L2.

15 Claims, 28 Drawing Sheets

(56) References Cited

U.S. PATENT DOCUMENTS

| | | | |
|---|---|---|---|
| 6,985,307 B2* | 1/2006 | Do | 359/716 |
| 7,304,807 B2 | 12/2007 | Isono | |
| 2003/0210341 A1 | 11/2003 | Isono | |
| 2005/0057679 A1 | 3/2005 | Isono | |
| 2005/0225872 A1 | 10/2005 | Uzawa et al. | |
| 2008/0068729 A1 | 3/2008 | Asami | |
| 2009/0141364 A1* | 6/2009 | Baba | 359/648 |

FOREIGN PATENT DOCUMENTS

| | | |
|---|---|---|
| JP | 05-107470 | 4/1993 |
| JP | 05-307139 | 11/1993 |
| JP | 08-220430 | 8/1996 |
| JP | 10-115777 | 5/1998 |
| JP | 10-300907 | 11/1998 |
| JP | 11-052227 | 2/1999 |
| JP | 2000-089105 | 3/2000 |
| JP | 2000-162498 | 6/2000 |
| JP | 2001-272598 | 10/2001 |
| JP | 2002-098889 | 4/2002 |
| JP | 2002-350720 | 12/2002 |
| JP | 2004-163849 | 6/2004 |
| JP | 2004-163850 | 6/2004 |
| JP | 2004-337346 | 12/2004 |
| JP | 2005-250512 | 9/2005 |
| JP | 2005-250513 | 9/2005 |
| JP | 2005-258467 | 9/2005 |
| JP | 2008-102500 | 5/2008 |
| JP | 2009-136387 | 6/2009 |
| WO | WO 2004/102247 | 11/2004 |

OTHER PUBLICATIONS

Chinese Office Action, dated Mar. 27, 2013, issued in corresponding Chinese Patent Application No. 201080023306.9.

* cited by examiner

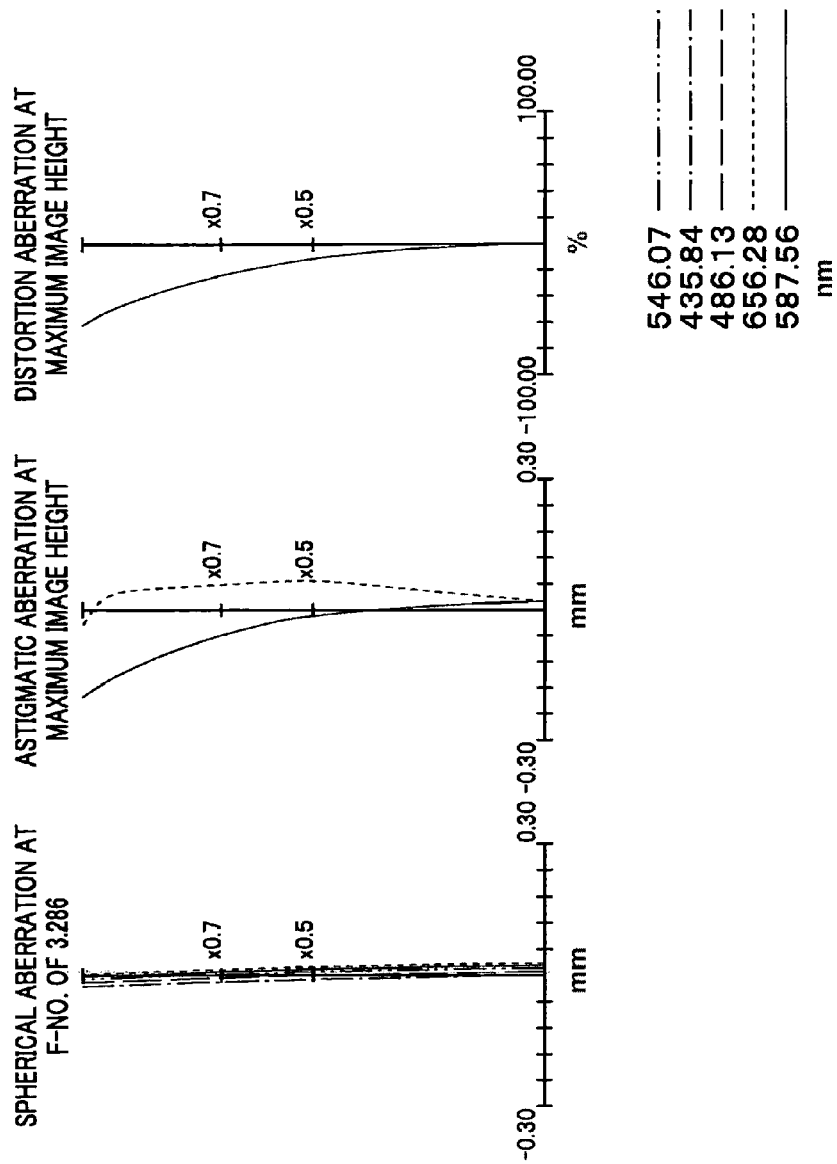

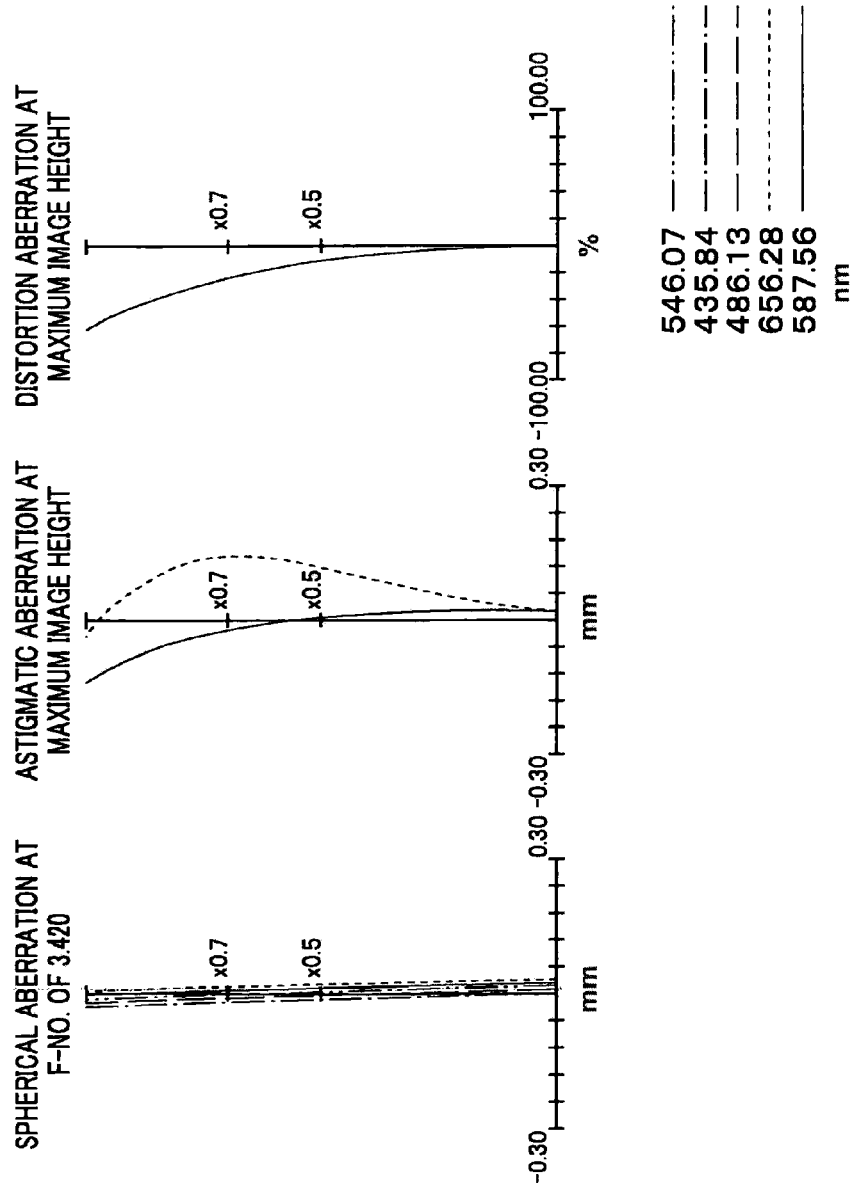

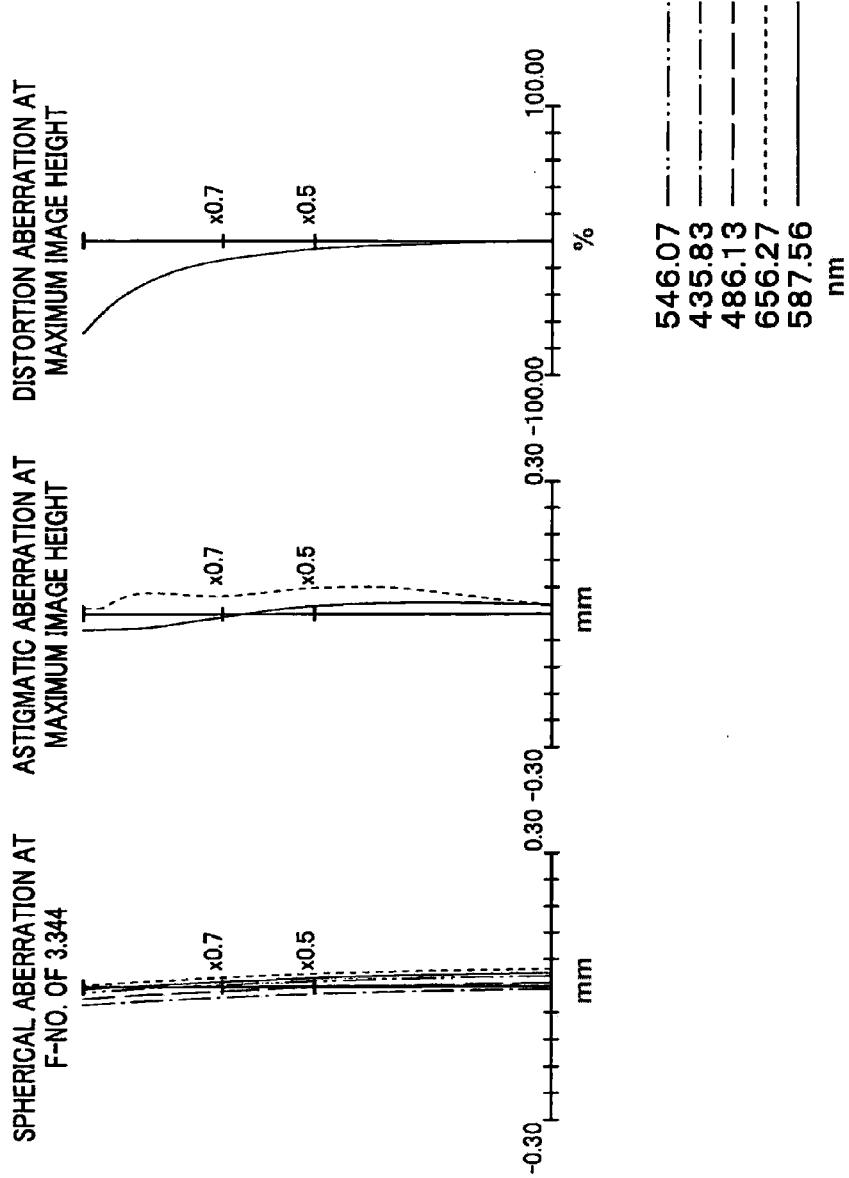

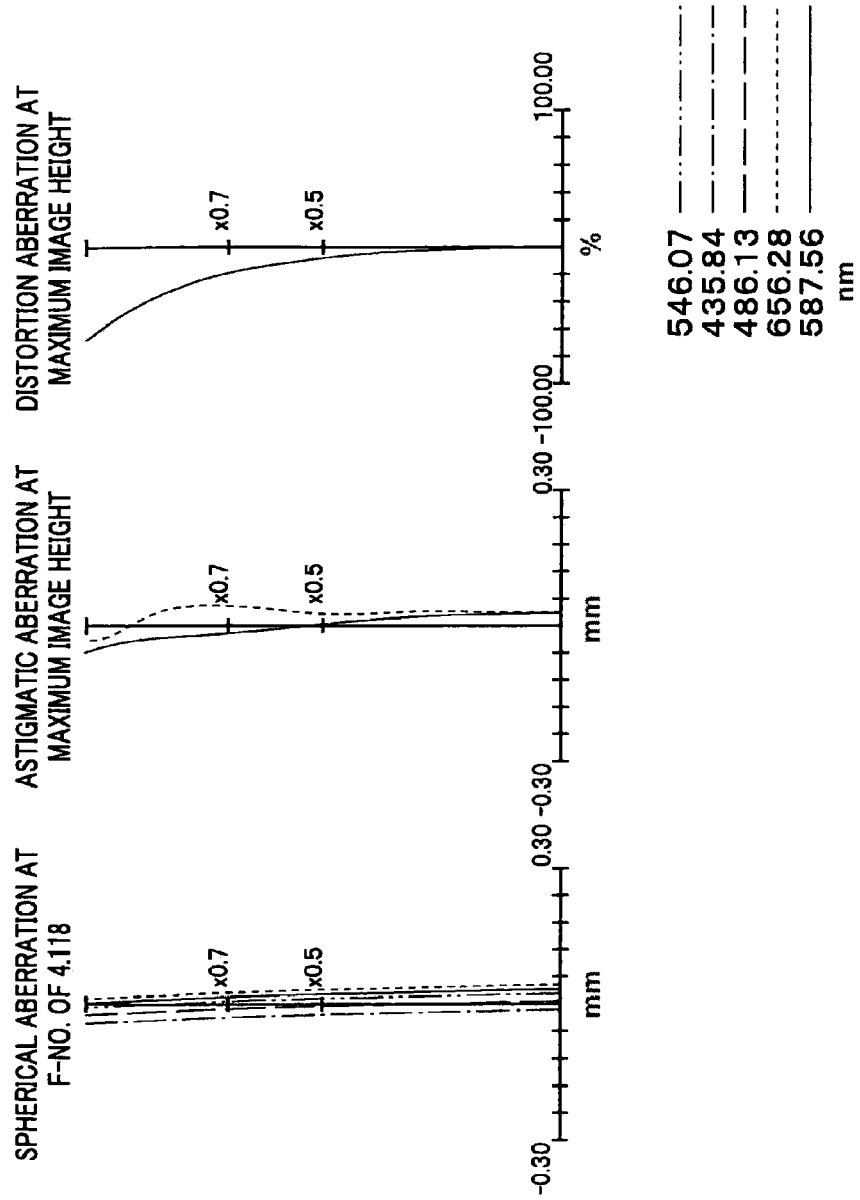

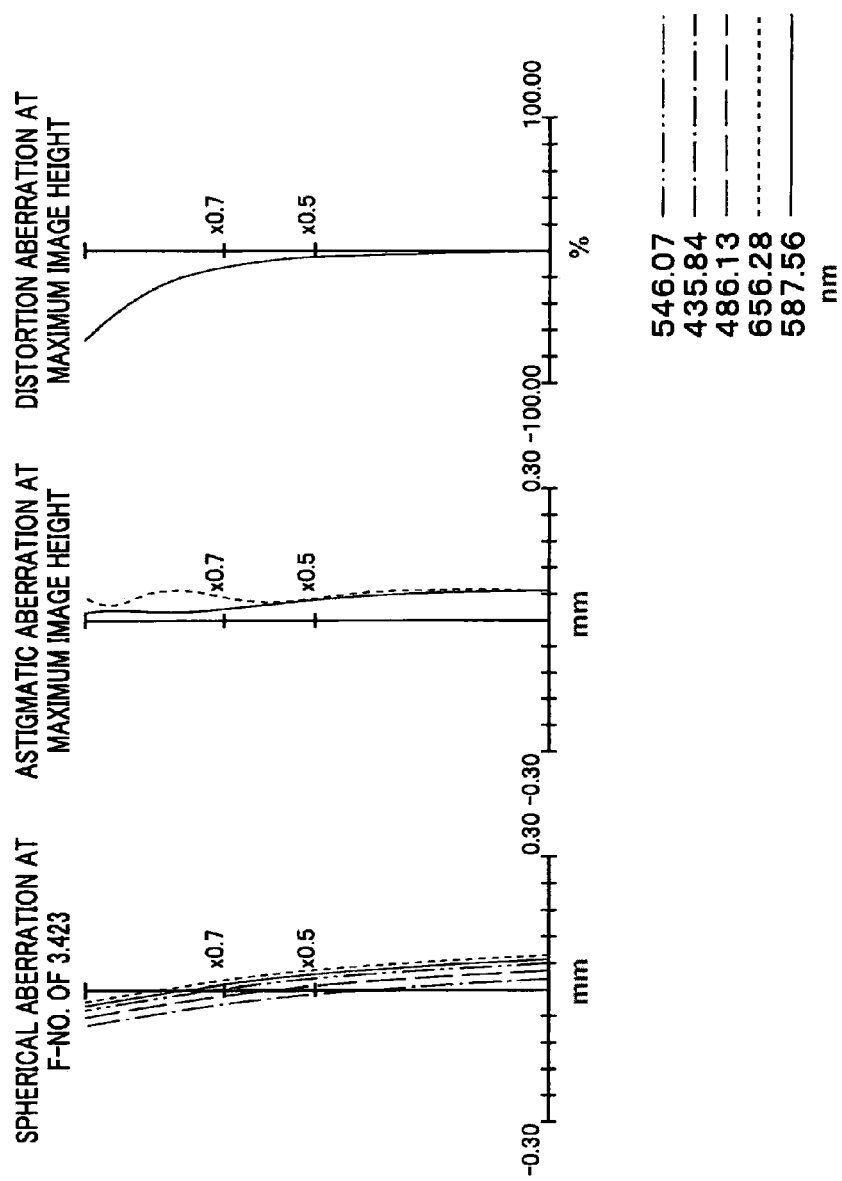

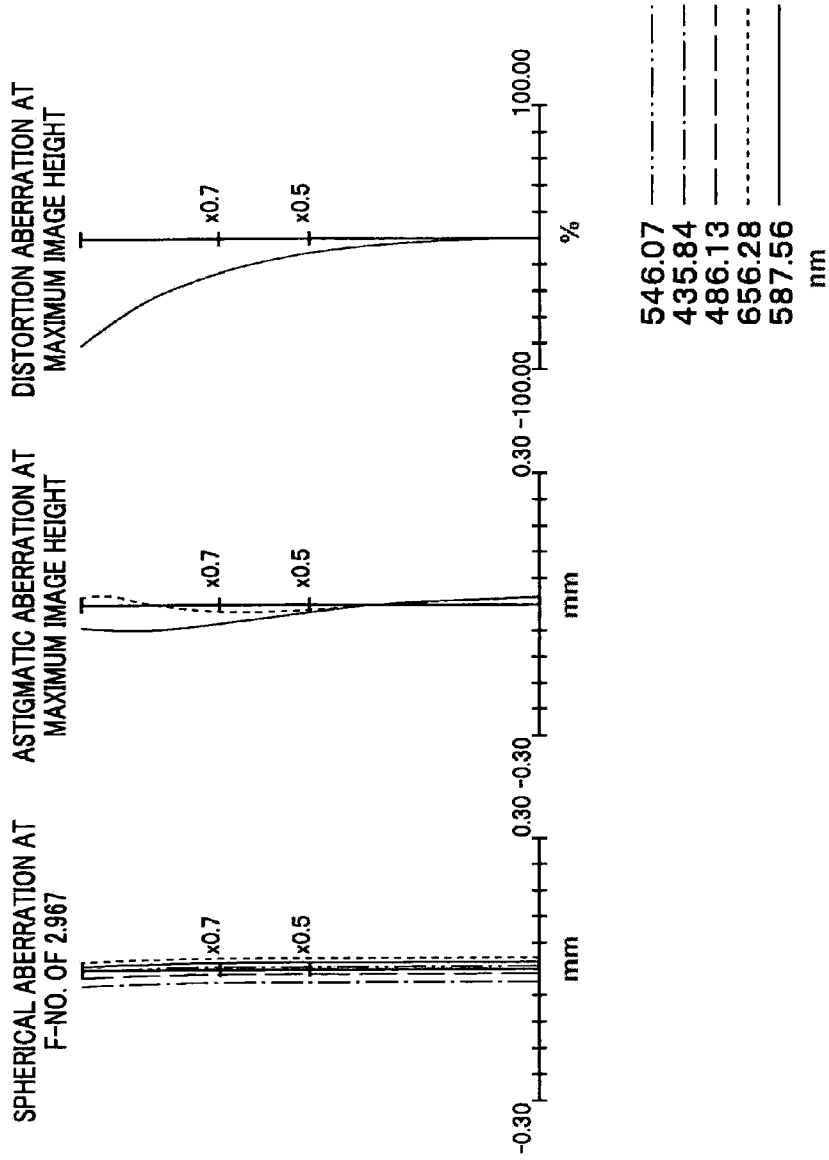

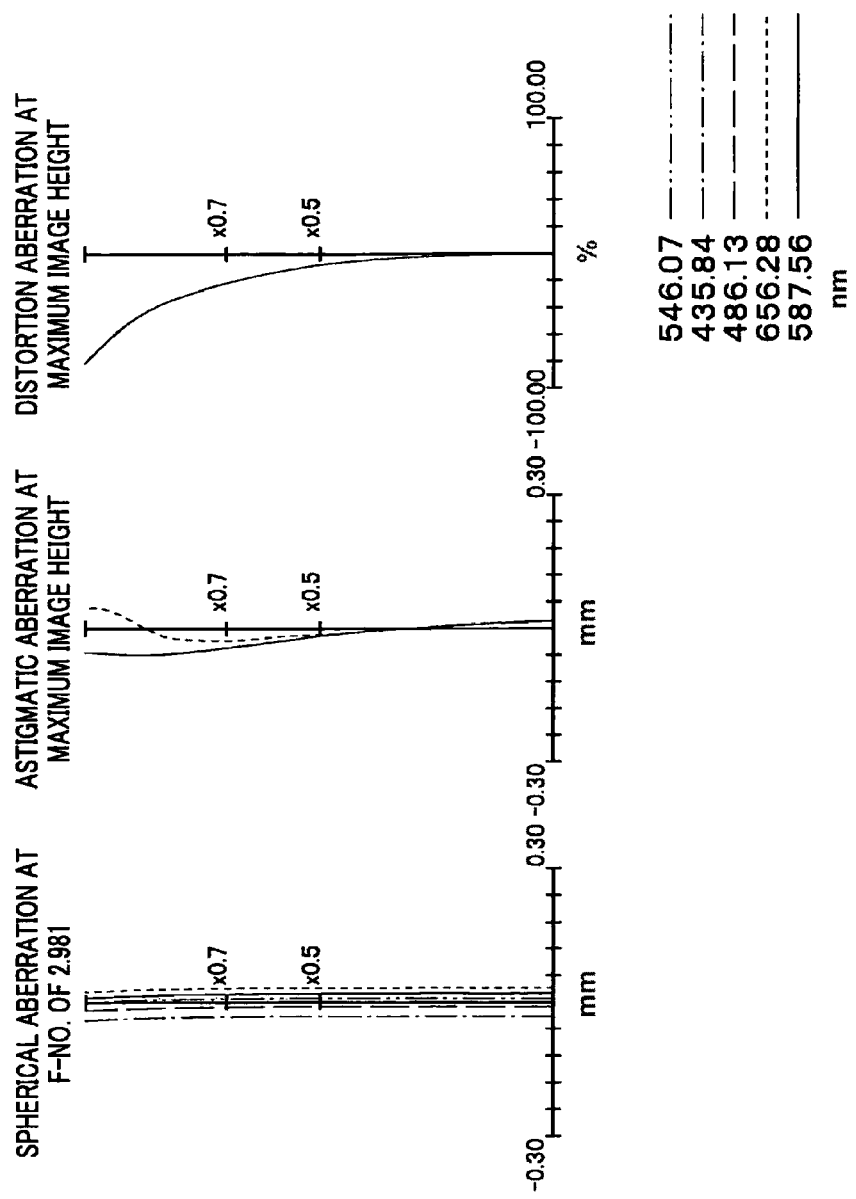

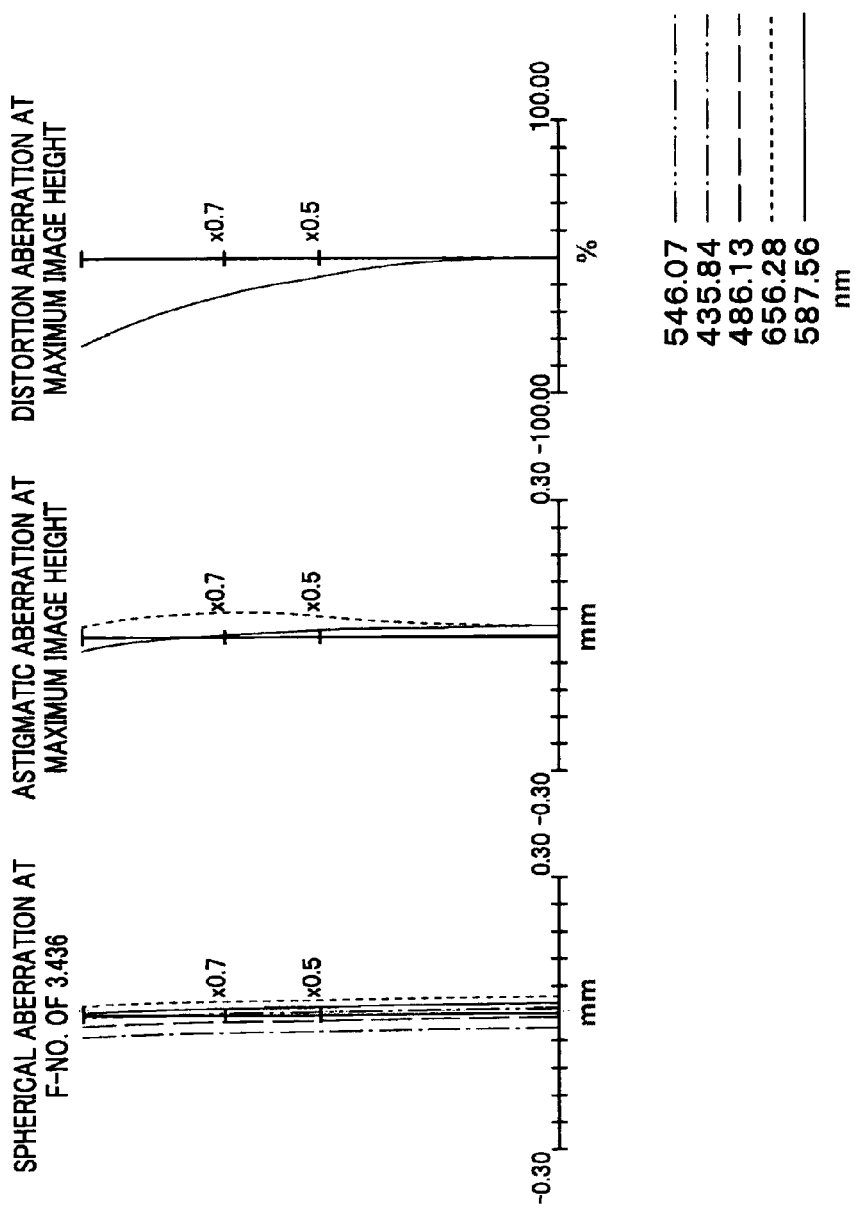

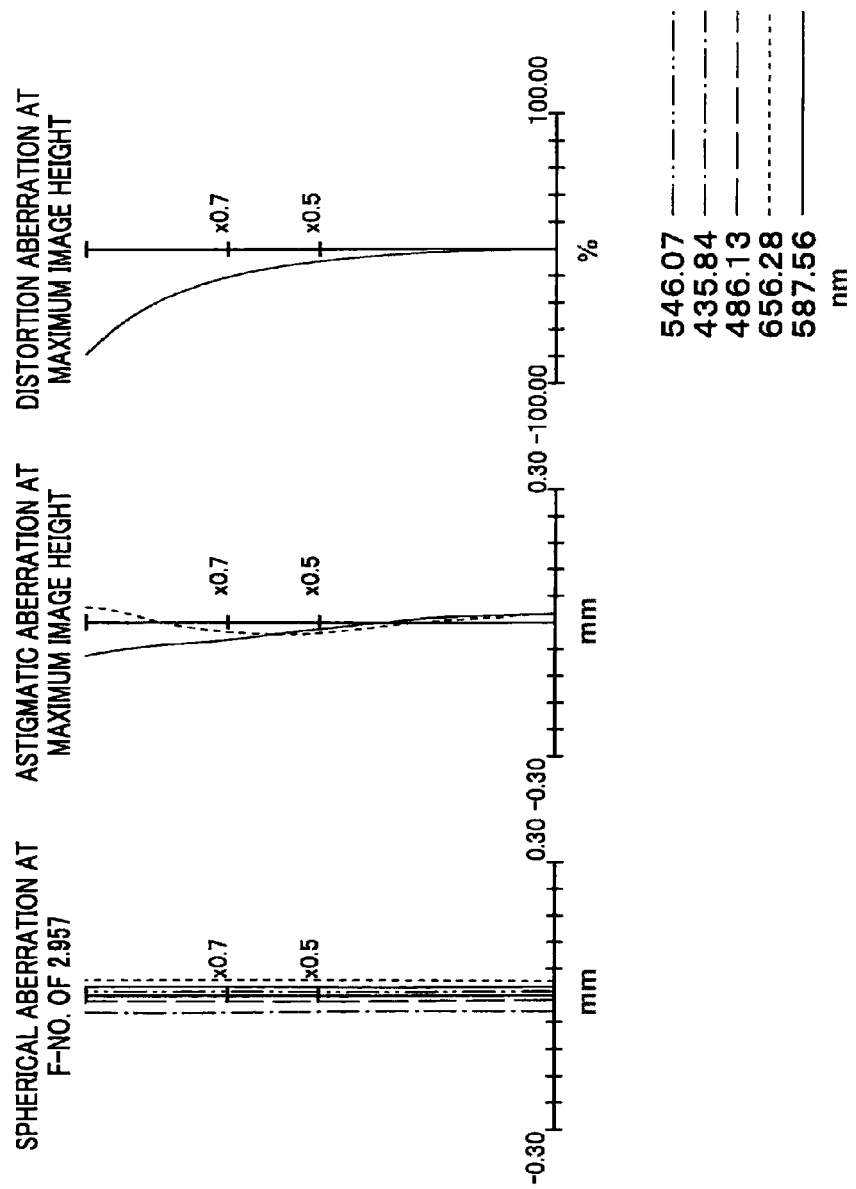

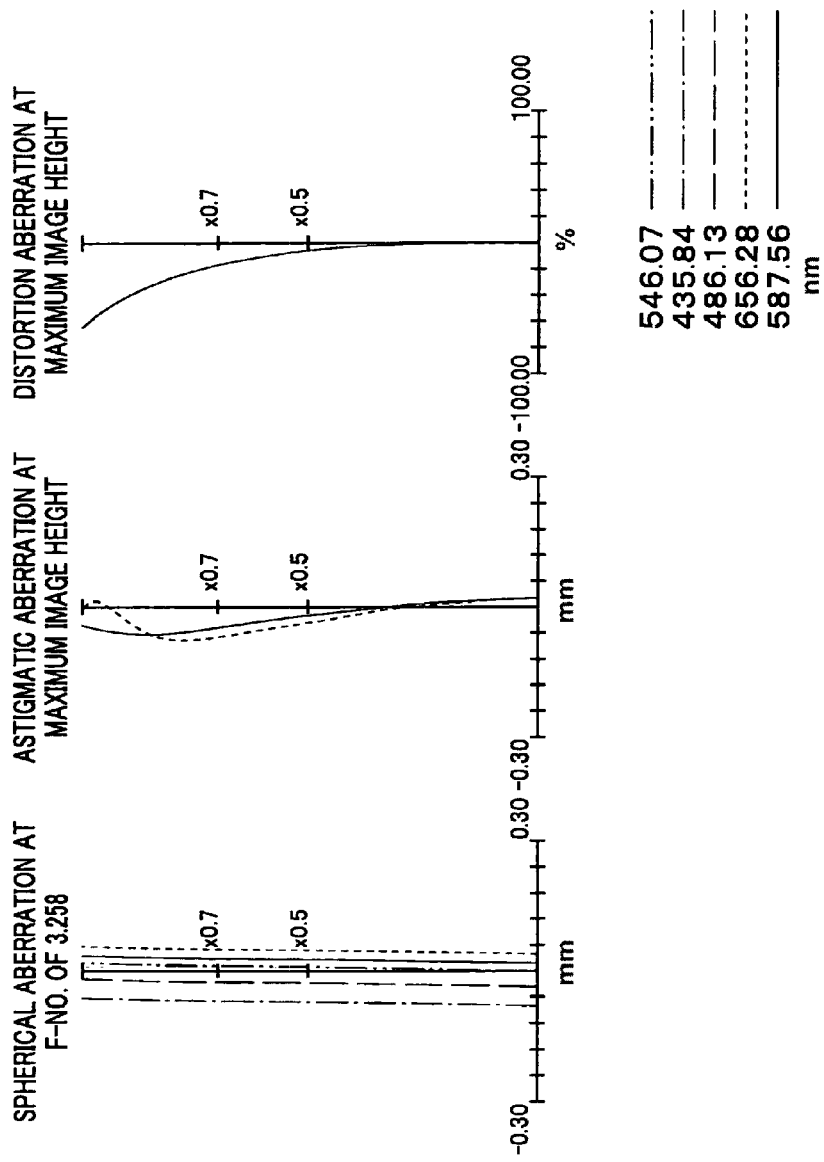

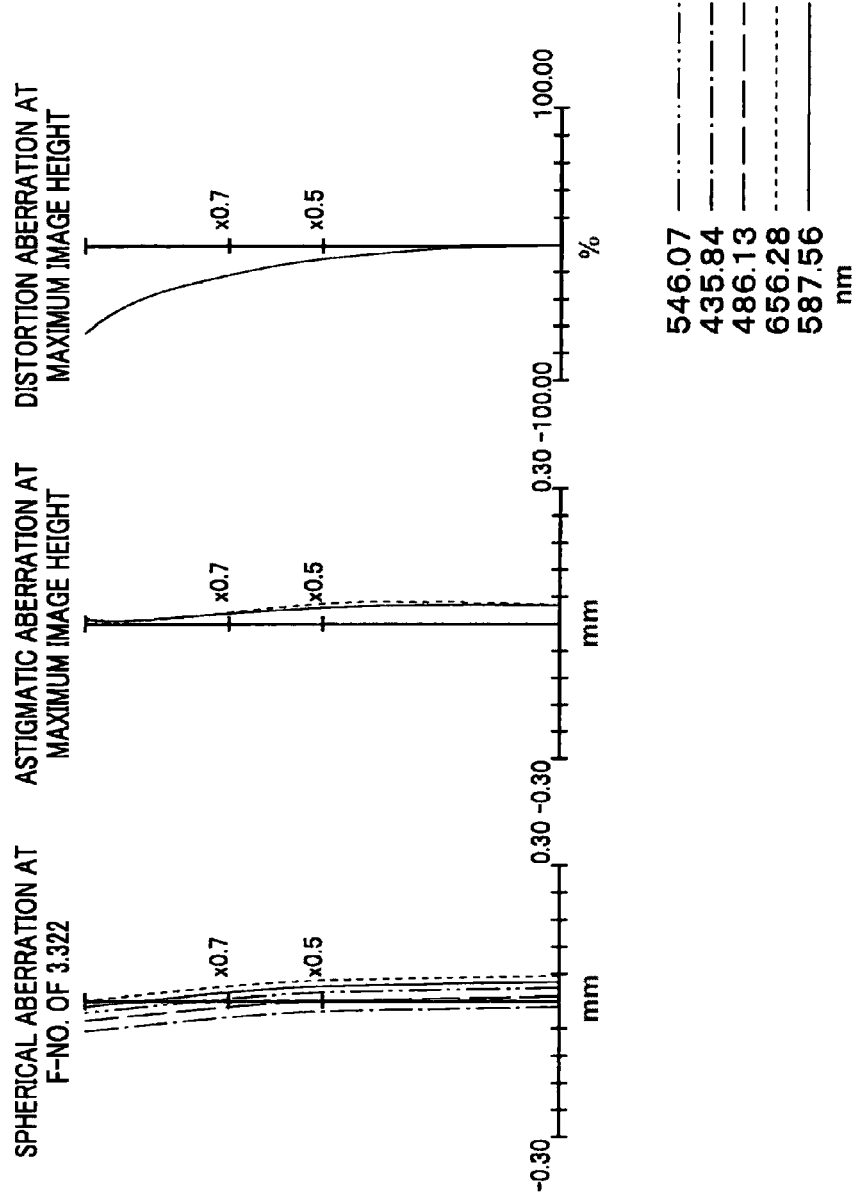

OBJECTIVE OPTICAL SYSTEM

CROSS REFERENCE TO RELATED APPLICATION

This application is a continuation application of PCT/JP2010/062058 filed on Jul. 16, 2010 and claims benefit of Japanese Application No. 2009-201824 filed in Japan on Sep. 1, 2009, the entire contents of which are incorporated herein by this reference.

BACKGROUND OF THE INVENTION

1. Field of the Invention

The present invention relates to an objective optical system, and more particularly, to an objective optical system which has a wide angle of view and can be used in endoscopes and the like.

2. Description of the Related Art

Conventionally, various techniques have been proposed to reduce components in objective optical systems for endoscopes or objective optical systems for digital cameras and thereby reduce costs.

As an example of such techniques, Japanese Patent Application Laid-Open Publication No. 5-307139 describes a retrofocus, substantially telecentric lens system which includes a negative first group, an aperture stop, a positive second group, and a positive third group, and has an aspheric surface on an image side of the second group or an object side of the third group. This provides a bright endoscopic objective lens which is made up of a small number of lenses and whose field curvature has been corrected properly.

Also, Japanese Patent Application Laid-Open Publication No. 2002-350720 describes a fixed-focal-length lens made up of a low-power first lens, at least one surface of which is aspheric; a second lens which has a convex-shaped surface on the image side and has positive refractive power; and a low-power third lens at least one surface of which is aspheric, where the lenses are arranged in this order starting from the object side. The lens system is capable of sufficiently good aberration correction as well as capable of achieving miniaturization and low costs using a three-lens configuration in which the second lens provided with an image-forming function is sandwiched between the first lens and third lens which have almost no power and function as corrector plates.

SUMMARY OF THE INVENTION

According to one aspect of the present invention, there is provided an objective optical system comprising, in order from an object side, a negative-powered first group, an aperture stop, a positive-powered second group, and a third group, wherein: a surface of the first group which is closest to an image side is a concave surface turned toward the image side; a surface of the second group which is closest to the image side is an aspheric surface; a surface of the third group which is closest to the object side is a convex surface turned toward the object side; the objective optical system has a three-group, three-lens configuration in which each group is made up of a single lens and all surfaces of the three lenses have power; and a distance between the second group and the third group is smaller than a distance between the first group and the second group, satisfying a conditional expression below $$d\_L23/d\_L12 < 0.25$$

$$1.7 < f\_L3/f\_L2$$

where $d\_L23$ is the distance between the second group and the third group, $d\_L12$ is the distance between the first group and the second group, $f\_L2$ is a focal length of the second group, and $f\_L3$ is a focal length of the third group.

According to another aspect of the present invention, there is provided an endoscopic objective optical system comprising: the objective optical system; and a cover placed closer to the object side than a surface of the first group which is closest to the object side.

BRIEF DESCRIPTION OF THE DRAWINGS

FIG. 1C is an aberration diagram of the objective optical system according to example 1 of the embodiment;

FIG. 2C is an aberration diagram of the objective optical system according to example 2 of the embodiment;

FIG. 3C is an aberration diagram of the objective optical system according to example 3 of the embodiment;

FIG. 5C is an aberration diagram of the objective optical system according to example 5 of the embodiment;

FIG. 6C is an aberration diagram of the objective optical system according to example 6 of the embodiment;

FIG. 7C is an aberration diagram of the objective optical system according to example 7 of the embodiment;

FIG. 8C is an aberration diagram of the objective optical system according to example 8 of the embodiment;

FIG. 9C is an aberration diagram of the objective optical system according to example 9 of the embodiment;

FIG. 10C is an aberration diagram of the objective optical system according to example 10 of the embodiment;

FIG. 12C is an aberration diagram of the objective optical system according to example 12 of the embodiment;

FIG. 13C is an aberration diagram of the objective optical system according to example 13 of the embodiment;

DETAILED DESCRIPTION OF THE PREFERRED EMBODIMENT(S)

An embodiment of the present invention will be described below with reference to the drawings.

Embodiment

FIGS. 1A to 16 show an embodiment of the present invention.

An objective optical system according to the present embodiment includes, in order from an object side, a negative-powered first group, a lens stop, a positive-powered second group, and a third group. A surface of the first group which is closest to an image side is a concave surface, a surface of the second group which is closest to the image side is an aspheric surface, and a surface of the third group which is closest to the object side is a convex surface. The second group and the third group are placed close to each other such that a distance between the second group and the third group will be smaller than a distance between the first group and the second group.

A configuration of the objective optical system will be described concretely with reference to FIG. 16 as follows.

Figure 16:
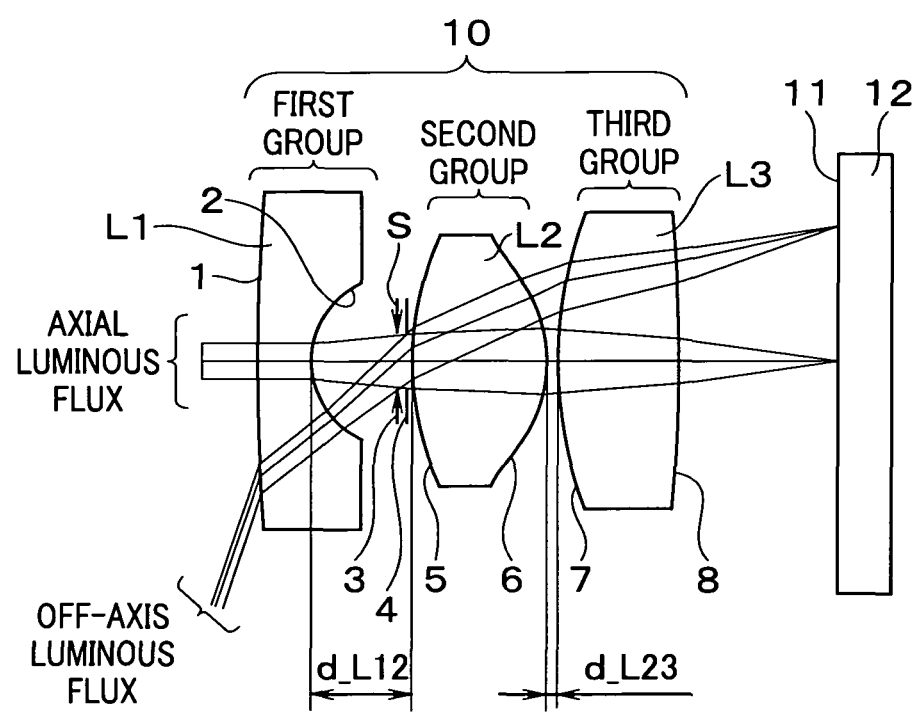
FIG. 16 is a diagram showing a schematic configuration of the objective optical system according to the embodiment.

In an objective optical system 10 shown in FIG. 16, each group is made up of a single lens: the first group includes a first lens L1, the second group includes a second lens L2, and the third group includes a third lens L3. A lens stop S is placed between the first lens L1 and the second lens L2. Furthermore, in the example shown in FIG. 16, an image pickup surface 11 of an image pickup device 12 is placed at an image plane position of the objective optical system 10.

Optical surfaces of the objective optical system 10 are as follows, in order from the object side.

That is, surface 1 is an object-side surface of the first lens L1, surface 2 is an image-side surface of the first lens L1, surface 3 is the lens stop S, surface 4 is an entrance pupil, surface 5 is an object-side surface of the second lens L2, surface 6 is an image-side surface of the second lens L2, surface 7 is an object-side surface of the third lens L3, and surface 8 is an image-side surface of the third lens L3. However, regarding surface 3 and surface 4, in some of the examples described later, the entrance pupil is surface 3 and the lens stop S is surface 4.

Surface 2 on the image side of the first lens L1 is a concave surface, surface 6 on the image side of the second lens L2 is an aspheric surface, and surface 7 on the object side of the third lens L3 is a convex surface. Furthermore, the objective optical system 10 is placed such that a distance d_L23 between surface 6 of the second lens L2 and surface 7 of the third lens L3 along an optical axis will be smaller than a distance d_L12 between surface 2 of the first lens L1 and surface 5 of the second lens L2 along the optical axis. Incidentally, a detailed conditional expression to be satisfied by the distance d_L12 and the distance d_L23 will be described later.

Next, optical functions of each group will be described below.

The first group is an element which mainly acts to implement a wide-angle capability. In particular, the surface on the object side plays a role in achieving the wide-angle capability (as can be seen from an off-axis luminous flux in the example shown in FIG. 16, on surface 1 on the object side of the first lens L1, incident light from a wide-angle side is refracted greatly in a direction of an image plane 11 (an incident angle is large and refracting angle is small)). In order to give a wide-angle capability to an objective optical system, it is necessary to reduce a focal length of the entire system, but if the focal lengths are reduced with use of only positive-powered groups, strong field curvature will occur. Therefore, to implement a wide-angle capability while correcting field curvature, it is necessary to place a negative-powered group in the optical system. In so doing, to reduce the number of lenses and downsize the optical system, limited placement locations are available, and desirably a negative-powered group is placed on the object side of the lens stop. Thus, according to the present embodiment, the first group closest to the object side is a negative-powered group.

The second group is an element which mainly has an image-forming function and an aberration correction effect. Since the first group has negative power as described above, a luminous flux passing through the first group becomes a diverging luminous flux (as can be seen from an axial luminous flux and an off-axis luminous flux in the example shown in FIG. 16, a luminous flux emitted from the first lens L1 diverges with an expanded flux width). Therefore, to change the diverging luminous flux into converging light, it is necessary to give relatively high positive power to the second group. However, it is known that high-power lenses are generally prone to aberrations. Thus, according to the present embodiment, an aspheric surface is used as the surface of the second group which is closest to the image side (surface 6 in the example shown in FIG. 16) to minimize generation of aberrations.

The third group is an element which mainly acts to maximize efficiency of incidence on the image pickup device, and in particular, plays a role in performing control so that the surface (surface 8 in the example shown in FIG. 16) on the image side will provide an incidence angle suitable for characteristics (described later) of the image pickup device. However, if the third group is used for aberration correction, it becomes difficult to control the incidence angle on the image pickup device. Thus, according to the present embodiment, the third group has relatively low power.

Next, arrangement of the groups will be described.

The distance between the first group and the second group is set to be large (i.e., the first group and the second group are placed away from each other) in order to enhance a wide-angle effect of the first group. That is, to refract a beam efficiently, it is advisable to place the lenses so as to cause the beam to pass through an outer region of the lenses. Thus, according to the present embodiment, a distance from the surface (surface 1 in the example shown in FIG. 16) of the first group which is closest to the object side to a surface of the lens stop is increased. Consequently, when passing through the first group, the beam passes through an outer part of the lens, and a wide-angle capability may be achieved efficiently.

On the other hand, the distance between the second group and the third group is minimized. This is because reducing the distance between the second group and the third group reduces the focal length of the objective optical system, giving a wide-angle capability to the objective optical system.

Thus, in the present embodiment, to implement the wide-angle capability efficiently, the distance between the first group and the second group is increased and the distance between the second group and the third group is reduced. In this way, after the distance between the second group and the third group is minimized, the distance between the first group and the second group is optimized. This eliminates the need to increase the distance between the second group and the third group more than necessary, making it possible to implement the wide-angle capability while keeping the total length to a minimum.

Furthermore, if the following conditional expression is satisfied, even when a low-refractive-index material such as resin is used, the distances among the groups can be set in a balanced manner, allowing the wide-angle capability to be implemented with the total length kept to a minimum.

$$d\_L23/d\_L12<0.25$$

where d_L23 is the distance between the second group and the third group and d_L12 is the distance between the first group and the second group.

Also, with recent image pickup devices, it is common practice to provide a microlens, a color filter, or the like on an image pickup surface on which multiple photo diodes for photoelectric conversion are arrayed, where the microlens is provided to increase an aperture ratio and the color filter is provided to implement a single color image pickup device. Light passing through the objective optical system and entering such an image pickup device, for example, at a large incident angle may be kicked by edges of the microlens or color filter, thereby failing to reach the image pickup surface. Consequently, an outer part of an image resulting from the large incident angle undergoes less photoelectric conversion than a central part of the image, causing a phenomenon in which an outer region of the image becomes dark. In this way, it is known that image pickup devices vary in characteristics depending on the incident angle of a light flux. Thus, according to the present embodiment, the darkening of the outer region of the image is bettered by controlling the incident angle on the image pickup device using the third group.

In addition, if the lenses are arranged so as to satisfy the following conditional expression, the incident angle on the image pickup device can be controlled efficiently using the third group while performing sufficient aberration correction using the second group.

$$1.7<f\_L3/f\_L2$$

where f_L2 is the focal length of the second group, and f_L3 is the focal length of the third group.

To achieve a wide angle of view using an inexpensive, but low-refractive-index material such as resin, it is advisable to give power to all the surfaces of all the lenses. Then, the number of lenses in each group can be reduced to one. Such configuration examples are shown in the examples described below as well as in the example shown in FIG. 16. Thus, it is possible to implement a wide-angle objective optical system with an angle of view of 130 degrees or more using a three-group, three-lens configuration.

Concrete examples of the objective optical system according to the present embodiment will be shown below. Incidentally, an aspheric expression as given by Expression 1 was used to calculate numeric data on the objective optical systems in the following examples.

$$Z = \frac{h^2}{R\{1 + \sqrt{1-(1+k)h^2/R^2}\}} + A_4 h^4 + A_6 h^6 + A_{10} h^{10} \quad \text{[Expression 1]}$$

where
Z: distance from an apex of an aspheric surface along an optical axis of the aspheric surface at a point at height h from the optical axis
h: height from the optical axis
k: conical constant
A4 to 10: fourth- to tenth-order aspheric coefficients
R: paraxial radius of curvature Also, FIGS. 1B to 11B illustrate how an endoscopic objective optical system is configured by further placing a dome-shaped, negative-powered, transparent cover 13 closer to the object than is the first group of the objective optical system to improve insertability of an endoscope or a capsule endoscope. Tables 1B to 11B show numeric data obtained when the dome-shaped cover 13 is placed. Object position in Tables 1B to 11B is the distance from the surface apex of the surface of the dome-shaped cover 13 which is located on the object side.

Example 1

Figure 1A:
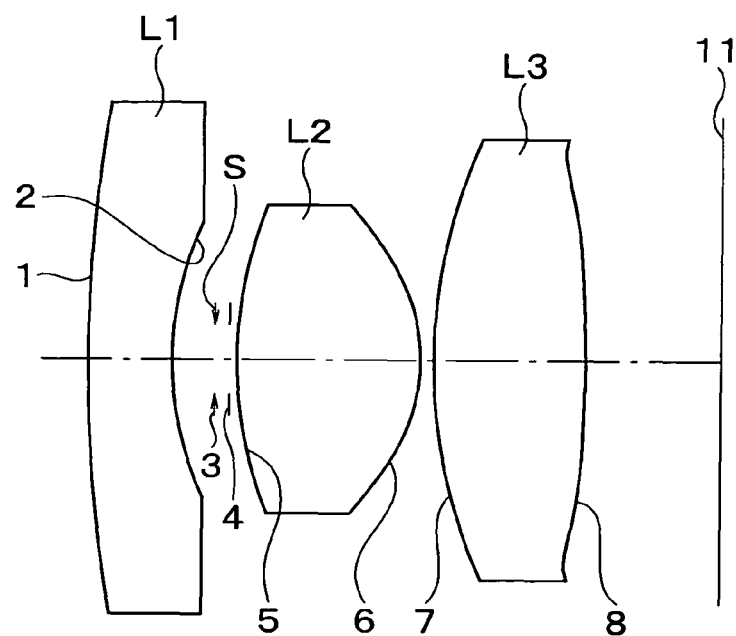
FIG. 1A is a sectional view of an objective optical system according to example 1 of an embodiment of the present invention.
Figure 1B:
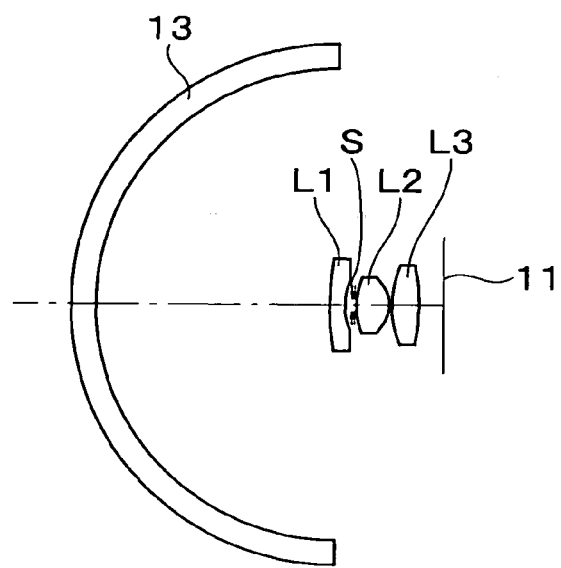
FIG. 1B is a sectional view taken when a negative-powered, dome-shaped cover is placed on an object side of the objective optical system according to example 1 of the embodiment.

FIG. 1A is a sectional view of an objective optical system according to example 1 of the present embodiment. FIG. 1B is a sectional view taken when the negative-powered, dome-shaped cover is placed on the object side of the objective optical system according to example 1 of the present embodiment. FIG. 1C is an aberration diagram of the objective optical system according to example 1 of the present embodiment. Table 1A shows numeric data on the objective optical system according to example 1 of the present embodiment. Table 1B shows numeric data obtained when the negative-powered, dome-shaped cover was placed on the object side of the objective optical system according to example 1 of the present embodiment.

TABLE 1A

| Surface No. | R | D | Nd | Vd |
|---|---|---|---|---|
| Object position | INF | 14.1343 | | |
| 1 | 7.3896 | 0.3855 | 1.5311 | 56 |
| 2(Aspheric surface) | 1.5604 | 0.1939 | | |
| 3(Lens stop) | INF | 0.0694 | | |
| 4 | INF | 0.0353 | | |
| 5 | 2.0358 | 0.8346 | 1.5311 | 56 |
| 6(Aspheric surface) | −0.7486 | 0.0600 | | |
| 7 | 2.5058 | 0.6926 | 1.5311 | 56 |
| 8(Aspheric surface) | −14.1650 | 0.6198 | | |
| Image location | INF | | | |

Aspheric surface data

| Surface No. | K | A4 | A6 | A8 | A10 |
|---|---|---|---|---|---|
| 2 | 0.045721 | 1.0945E−01 | −1.3813E−01 | −4.3160E−01 | |
| 6 | −1.3527 | −4.4434E−02 | −4.4789E−02 | 3.0478E−01 | 3.1421E−05 |
| 8 | 9.5581 | −1.3634E−01 | −1.3881E−03 | 8.4316E−02 | 3.8101E−06 |

| | |
|---|---|
| Focal length of entire system | 1.0000 |
| Focal length of first lens | −3.7961 |
| Focal length of second lens | 1.1456 |
| Focal length of third lens | 4.0505 |
| Effective f-No. | 3.3638 |
| Center magnification | −0.07020 |
| Front focus position | 0.1106 |
| Rear focus position | −0.0551 |
| Maximum image height | 1.0074 |
| Half view angle at maximum image height | −69.05 |
| Incident angle on image pickup device at maximum image height | −10.63 |
| d_L23/d_L12 | 0.201 |
| |f_L3/f_L2| | 3.536 |

TABLE 1B

| Surface No. | R | D | Nd | Vd |
|---|---|---|---|---|
| Object position | | 9.1231 | | |
| Object-side surface of dome | 6.9387 | 0.6425 | 1.585 | 30 |
| Image-side surface of dome | 6.2962 | 6.1292 | | |
| Object-side surface of first lens | 7.3896 | 0.3855 | 1.5311 | 56 |

| | |
|---|---|
| Focal length of entire system | 1.0003 |
| Focal length of dome | −183.331 |
| Effective f-No. | 3.3607 |
| Center magnification | −0.06250 |
| Front focus position | 6.8822 |
| Rear focus position | −0.0497 |
| Half view angle at maximum image height | −69.08 |

TABLE 1B-continued

| | |
|---|---|
| Incident angle on image pickup device at maximum image height | −10.63 |
| |f_d/f| | 183.331 |

Example 2

Figure 2A:
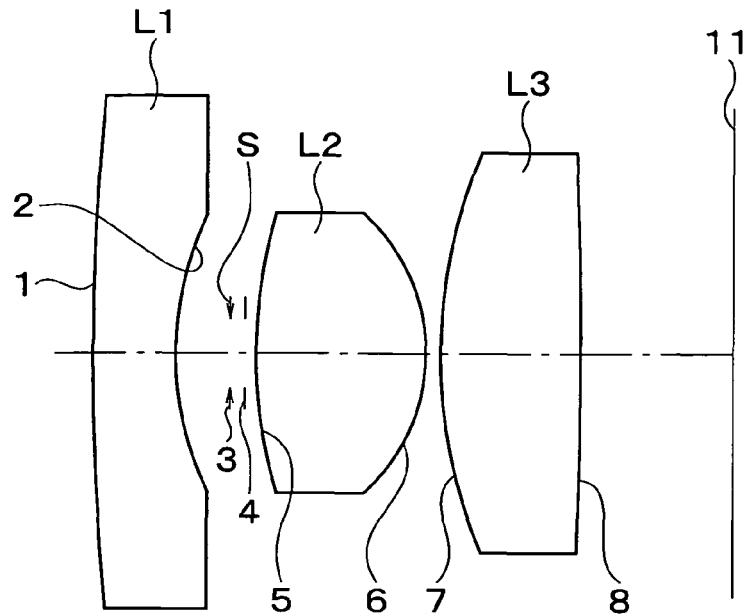
FIG. 2A is a sectional view of an objective optical system according to example 2 of the embodiment.
Figure 2B:
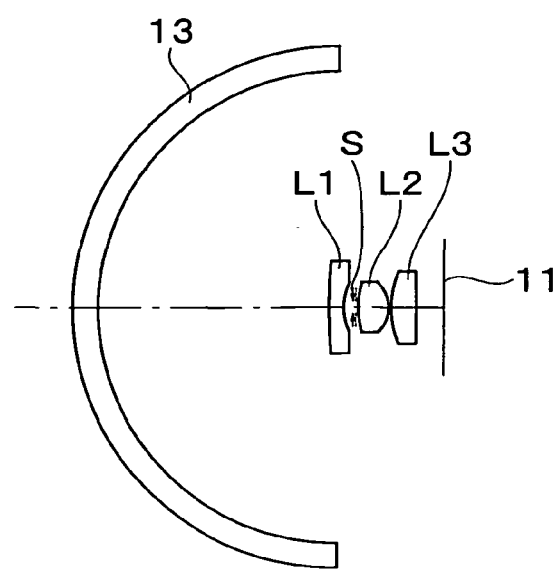
FIG. 2B is a sectional view taken when the negative-powered, dome-shaped cover is placed on an object side of the objective optical system according to example 2 of the embodiment.

FIG. 2A is a sectional view of an objective optical system according to example 2 of the present embodiment. FIG. 2B is a sectional view taken when the negative-powered, dome-shaped cover is placed on the object side of the objective optical system according to example 2 of the present embodiment. FIG. 2C is an aberration diagram of the objective optical system according to example 2 of the present embodiment. Table 2A shows numeric data on the objective optical system according to example 2 of the present embodiment. Table 2B shows numeric data obtained when the negative-powered, dome-shaped cover was placed on the object side of the objective optical system according to example 2 of the present embodiment.

TABLE 2A

| Surface No. | R | D | N | V |
|---|---|---|---|---|
| Object position | INF | 11.8895 | | |
| 1 | 14.4669 | 0.3963 | 1.5311 | 56 |
| 2 | 1.6791 | 0.2510 | | |
| 3(Lens stop) | INF | 0.0713 | | |
| 4 | INF | 0.0396 | | |
| 5 | 2.6421 | 0.7926 | 1.5311 | 56 |
| 6(Aspheric surface) | −0.7385 | 0.0661 | | |

TABLE 2A-continued

| | | | | |
|---|---|---|---|---|
| 7 | 2.4532 | 0.6605 | 1.5311 | 56 |
| 8 | −22.6997 | 0.7134 | | |
| Image location | INF | | | |

Aspheric surface data

| Surface No. | K | A4 | A6 | A8 | A10 |
|---|---|---|---|---|---|
| 6 | −1.4115 | −1.1074E−01 | −5.4402E−02 | 2.7571E−01 | 3.1256E−03 |

| | |
|---|---|
| Focal length of entire system | 1.0000 |
| Focal length of first lens | −3.6003 |
| Focal length of second lens | 1.1782 |
| Focal length of third lens | 4.1892 |
| Effective f-No. | 3.5199 |
| Center magnification | −0.08306 |
| Front focus position | 0.1495 |
| Rear focus position | −0.0665 |
| Maximum image height | 1.0357 |
| Half view angle at maximum image height | −69.79 |
| Incident angle on image pickup device at maximum image height | −14.87 |
| d_L23/d_L12 | 0.182 |
| |f_L3/f_L2| | 3.556 |

TABLE 2B

| Surface No. | R | D | N | V |
|---|---|---|---|---|
| Object position | INF | 5.9448 | | |
| Object-side surface of dome | 7.1337 | 0.6605 | 1.585 | 30 |
| Image-side surface of dome | 6.4732 | 6.3014 | | |
| Object-side surface of first lens | 14.4669 | 0.3963 | 1.5311 | 56 |

| | |
|---|---|
| Focal length of entire system | 1.0001 |
| Focal length of dome | −188.484 |
| Effective f-No. | 3.5182 |
| Center magnification | −0.07660 |
| Front focus position | 7.1115 |
| Rear focus position | −0.0612 |
| Half view angle at maximum image height | −69.82 |
| Incident angle on image pickup device at maximum image height | −14.87 |
| |f_d/f| | 188.484 |

Example 3

Figure 3A:
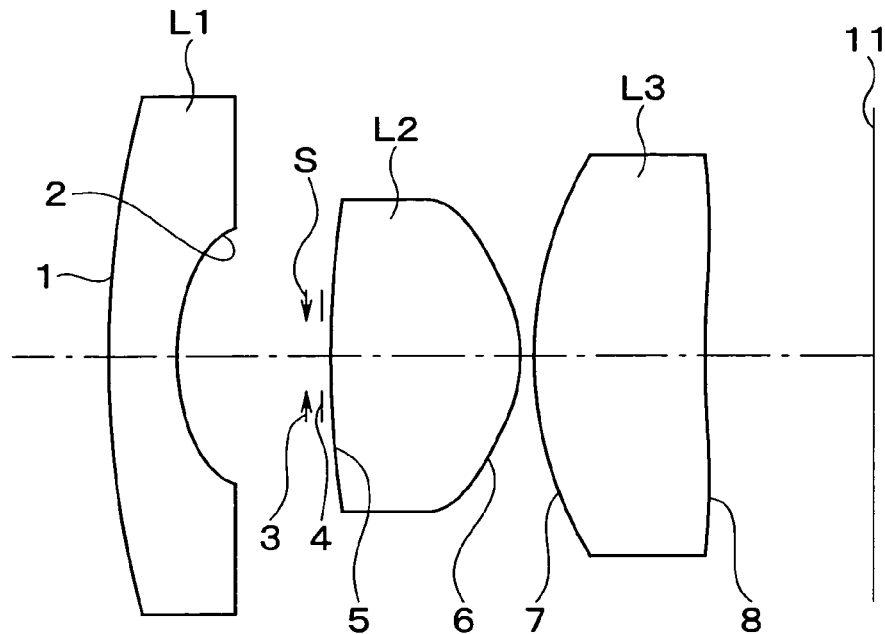
FIG. 3A is a sectional view of an objective optical system according to example 3 of the embodiment.
Figure 3B:
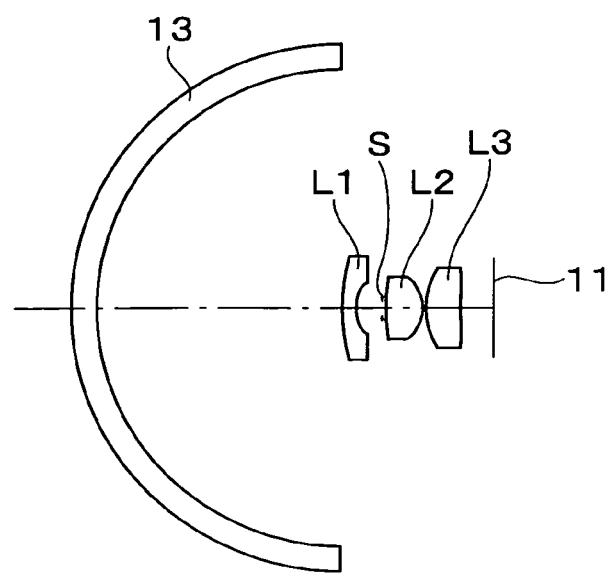
FIG. 3B is a sectional view taken when the negative-powered, dome-shaped cover is placed on an object side of the objective optical system according to example 3 of the embodiment.

FIG. 3A is a sectional view of an objective optical system according to example 3 of the present embodiment. FIG. 3B is a sectional view taken when the negative-powered, dome-shaped cover is placed on the object side of the objective optical system according to example 3 of the present embodiment. FIG. 3C is an aberration diagram of the objective optical system according to example 3 of the present embodiment. Table 3A shows numeric data on the objective optical system according to example 3 of the present embodiment. Table 3B shows numeric data obtained when the negative-powered, dome-shaped cover was placed on the object side of the objective optical system according to example 3 of the present embodiment.

TABLE 3A

| Surface No. | R | D | N | V |
|---|---|---|---|---|
| Object position | INF | 11.0521 | | |
| 1 | 5.6426 | 0.3725 | 1.5311 | 56 |
| 2(Aspheric surface) | 1.0454 | 0.6914 | | |
| 3(Lens stop) | INF | 0.0671 | | |
| 4 | INF | 0.0373 | | |
| 5 | 5.1280 | 0.9853 | 1.5311 | 56 |
| 6(Aspheric surface) | −0.8394 | 0.0744 | | |
| 7 | 1.9862 | 0.8983 | 1.5311 | 56 |
| 8(Aspheric surface) | 9.0286 | 0.8729 | | |
| Image location | INF | | | |

Aspheric surface data

| Surface No. | K | A4 | A6 | A8 |
|---|---|---|---|---|
| 2 | −1.5876 | 1.3440E−01 | −1.1830E+00 | 3.9155E+00 |
| 6 | 0.064393 | 1.6094E−01 | 5.9809E−01 | −1.2347E−01 |
| 8 | 64.337 | 1.1708E−01 | −3.6287E−01 | 1.6941E−01 |

| | |
|---|---|
| Focal length of entire system | 1.0000 |
| Focal length of first lens | −2.4755 |
| Focal length of second lens | 1.4348 |
| Focal length of third lens | 4.5714 |
| Effective f-No. | 3.4291 |
| Center magnification | −0.08641 |
| Front focus position | 0.5201 |
| Rear focus position | −0.0650 |
| Maximum image height | 0.9736 |
| Half view angle at maximum image height | −72.55 |
| Incident angle on image pickup device at maximum image height | −7.67 |
| d_L23/d_L12 | 0.094 |
| |f_L3/f_L2| | 3.186 |

TABLE 3B

| Surface No. | R | D | N | V |
|---|---|---|---|---|
| Object position | INF | 5.2156 | | |
| Object-side surface of dome | 6.7058 | 0.6209 | 1.585 | 30 |
| Image-side surface of dome | 6.0849 | 5.9235 | | |
| Object-side surface of first lens | 5.6426 | 0.3725 | 1.5311 | 56 |

| | |
|---|---|
| Focal length of entire system | 0.9980 |
| Focal length of dome | −177.170 |
| Effective f-No. | 3.4294 |
| Center magnification | −0.08127 |
| Front focus position | 7.0637 |
| Rear focus position | −0.0594 |
| Half view angle at maximum image height | −72.64 |
| Incident angle on image pickup device at maximum image height | −7.67 |
| |f_d/f| | 177.17 |

Example 4

Figure 4A:
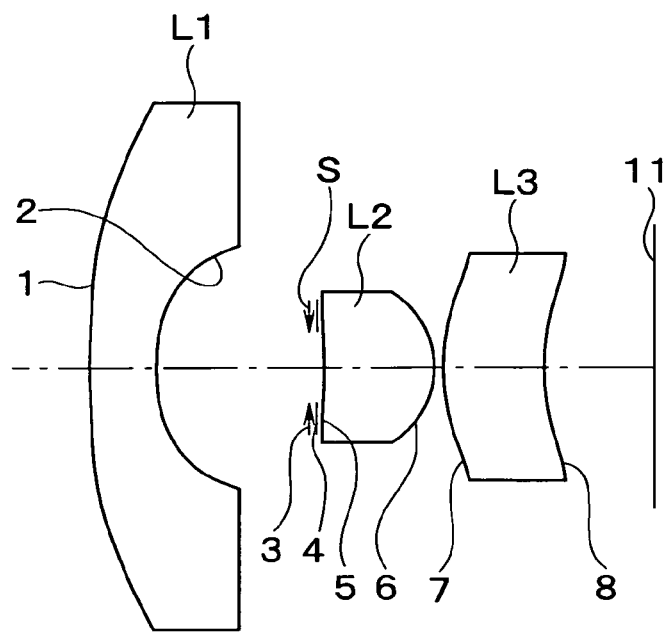
FIG. 4A is a sectional view of an objective optical system according to example 4 of the embodiment.
Figure 4B:
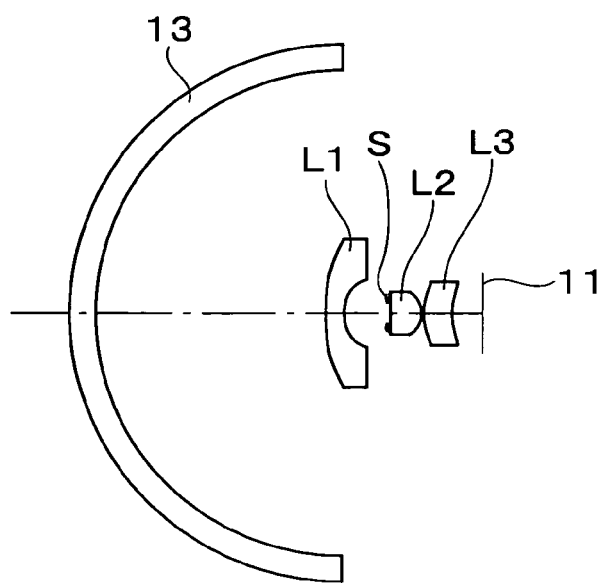
FIG. 4B is a sectional view taken when the negative-powered, dome-shaped cover is placed on an object side of the objective optical system according to example 4 of the embodiment.
Figure 4C:
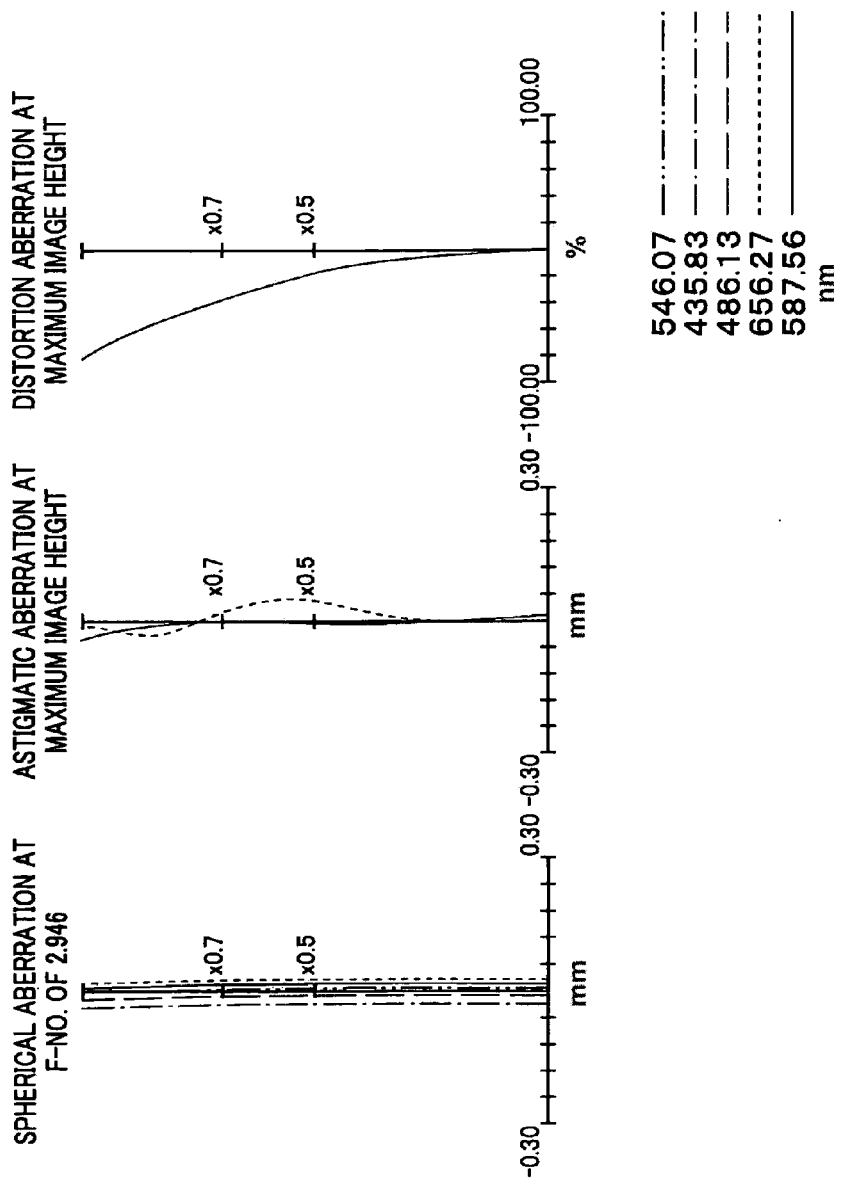
FIG. 4C is an aberration diagram of the objective optical system according to example 4 of the embodiment.

FIG. 4A is a sectional view of an objective optical system according to example 4 of the present embodiment. FIG. 4B is a sectional view taken when the negative-powered, dome-shaped cover is placed on the object side of the objective optical system according to example 4 of the present embodiment. FIG. 4C is an aberration diagram of the objective optical system according to example 4 of the present embodiment. Table 4A shows numeric data on the objective optical system according to example 4 of the present embodiment. Table 4B shows numeric data obtained when the negative-powered, dome-shaped cover was placed on the object side of the objective optical system according to example 4 of the present embodiment.

TABLE 4A

| Surface No. | R | D | N | V |
|---|---|---|---|---|
| Object position | INF | 16.5665 | | |
| 1(Aspheric surface) | 7.8209 | 0.5370 | 1.5311 | 56 |
| 2(Aspheric surface) | 1.4327 | 1.2892 | | |
| 3(Lens stop) | INF | 0.0540 | | |
| 4 | INF | 0.0540 | | |
| 5(Aspheric surface) | −7.8509 | 0.9104 | 1.5311 | 56 |
| 6(Aspheric surface) | −0.7221 | 0.0720 | | |
| 7(Aspheric surface) | 1.6493 | 0.8345 | 1.5311 | 56 |
| 8(Aspheric surface) | 1.4496 | 0.9004 | | |
| Image location | INF | | | |

| Aspheric surface data | | | |
|---|---|---|---|
| Surface No. | K | A4 | A6 |
| 1 | | 1.8868E−02 | −1.9652E−03 |
| 2 | | 5.5233E−02 | 2.2400E−01 |
| 5 | | −6.9578E−01 | |
| 6 | | 7.1635E−02 | 3.1279E−01 |
| 7 | | −1.0422E−01 | |
| 8 | | −2.5481E−01 | 3.5748E−02 |

| | |
|---|---|
| Focal length of entire system | 1.0000 |
| Focal length of first lens | −3.3876 |
| Focal length of second lens | 1.4277 |
| Focal length of third lens | 49.4865 |
| Effective f-No. | 3.0171 |
| Center magnification | −0.05721 |
| Front focus position | 0.9135 |

TABLE 4A-continued

| | |
|---|---|
| Rear focus position | −0.0526 |
| Maximum image height | 1.1453 |
| Half view angle at maximum image height | −81.46 |
| Incident angle on image pickup device at maximum image height | −17.60 |
| d_L23/d_L12 | 0.052 |
| |f_L3/f_L2| | 34.663 |

TABLE 4B

| Surface No. | R | D | N | V |
|---|---|---|---|---|
| Object position | INF | 10.4441 | | |
| Object-side surface of dome | 8.1032 | 0.9004 | 1.585 | 30 |
| Image-side surface of dome | 7.2028 | 6.6626 | | |
| Object-side surface of first lens | 7.8209 | 0.5370 | 1.5311 | 56 |

| | |
|---|---|
| Focal length of entire system | 0.9979 |
| Focal length of dome | −174.774 |
| Effective f-No. | 3.0186 |
| Center magnification | −0.05274 |
| Front focus position | 8.4757 |
| Rear focus position | −0.0469 |
| Half view angle at maximum image height | −81.53 |
| Incident angle on image pickup device at maximum image height | −17.60 |
| |f_d/f| | 174.774 |

Example 5

Figure 5A:
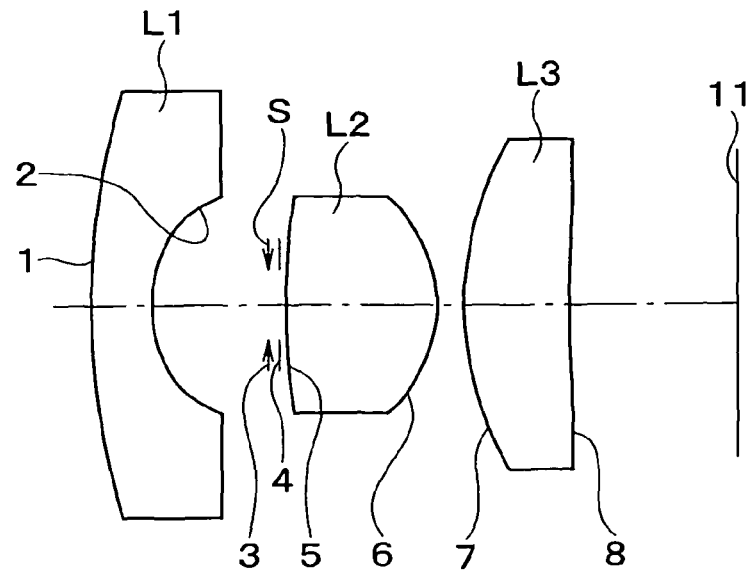
FIG. 5A is a sectional view of an objective optical system according to example 5 of the embodiment.
Figure 5B:
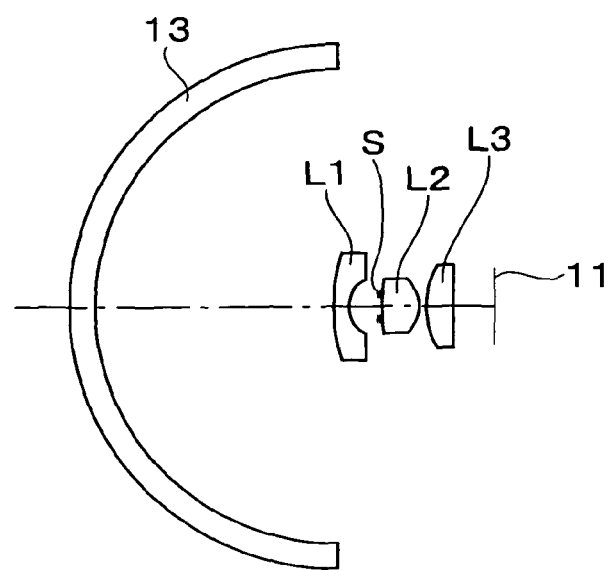
FIG. 5B is a sectional view taken when the negative-powered, dome-shaped cover is placed on an object side of the objective optical system according to example 5 of the embodiment.

FIG. 5A is a sectional view of an objective optical system according to example 5 of the present embodiment. FIG. 5B is a sectional view taken when the negative-powered, dome-shaped cover is placed on the object side of the objective optical system according to example 5 of the present embodiment. FIG. 5C is an aberration diagram of the objective optical system according to example 5 of the present embodiment. Table 5A shows numeric data on the objective optical system according to example 5 of the present embodiment. Table 5B shows numeric data obtained when the negative-powered, dome-shaped cover was placed on the object side of the objective optical system according to example 5 of the present embodiment.

TABLE 5A

| Surface No. | R | D | N | V |
|---|---|---|---|---|
| Object position | INF | 11.8486 | | |
| 1 | 5.2149 | 0.3742 | 1.5311 | 56 |
| 2(Aspheric surface) | 0.9042 | 0.7313 | | |
| 3(Lens stop) | INF | 0.0673 | | |
| 4 | INF | 0.0374 | | |
| 5 | 4.5599 | 0.9471 | 1.5311 | 56 |
| 6(Aspheric surface) | −0.8677 | 0.1704 | | |
| 7 | 1.9959 | 0.6694 | 1.5311 | 56 |
| 8(Aspheric surface) | 14.5387 | 1.0601 | | |
| Image location | INF | | | |

TABLE 5A-continued

Aspheric surface data

| Surface No. | K | A4 | A6 | A8 |
|---|---|---|---|---|
| 2 | −1.2612 | 3.4591E−02 | 8.7515E−01 | 1.9601E+00 |
| 6 | 0.46072 | 2.0354E−01 | 2.7578E−02 | 1.6001E+00 |
| 8 | −222.68 | 1.3935E−01 | −3.1091E−01 | 1.6170E−01 |

| | |
|---|---|
| Focal length of entire system | 1.0000 |
| Focal length of first lens | −2.1147 |
| Focal length of second lens | 1.4551 |
| Focal length of third lens | 4.2585 |
| Effective f-No. | 4.2105 |
| Center magnification | −0.08072 |
| Front focus position | 0.5400 |
| Rear focus position | −0.0597 |
| Maximum image height | 0.9778 |
| Half view angle at maximum image height | −72.22 |
| Incident angle on image pickup device at maximum image height | −10.00 |
| d_L23/d_L12 | 0.204 |
| |f_L3/f_L2| | 2.927 |

TABLE 5B

| Surface No. | R | D | N | V |
|---|---|---|---|---|
| Object position | INF | 6.2361 | | |
| Object-side surface of dome | 6.7350 | 0.6236 | 1.585 | 30 |

TABLE 5B-continued

| | | | | |
|---|---|---|---|---|
| Image-side surface of dome | 6.1114 | 5.9492 | | |
| Object-side surface of first lens | 5.2149 | 0.3742 | 1.5311 | 56 |

| | |
|---|---|
| Focal length of entire system | 0.9979 |
| Focal length of dome | −177.949 |
| Effective f-No. | 4.2095 |
| Center magnification | −0.07476 |
| Front focus position | 7.1120 |
| Rear focus position | −0.0541 |
| Half view angle at maximum image height | −72.31 |
| Incident angle on image pickup device at maximum image height | −10.00 |
| |f_d/f| | 177.949 |

Example 6

Figure 6A:
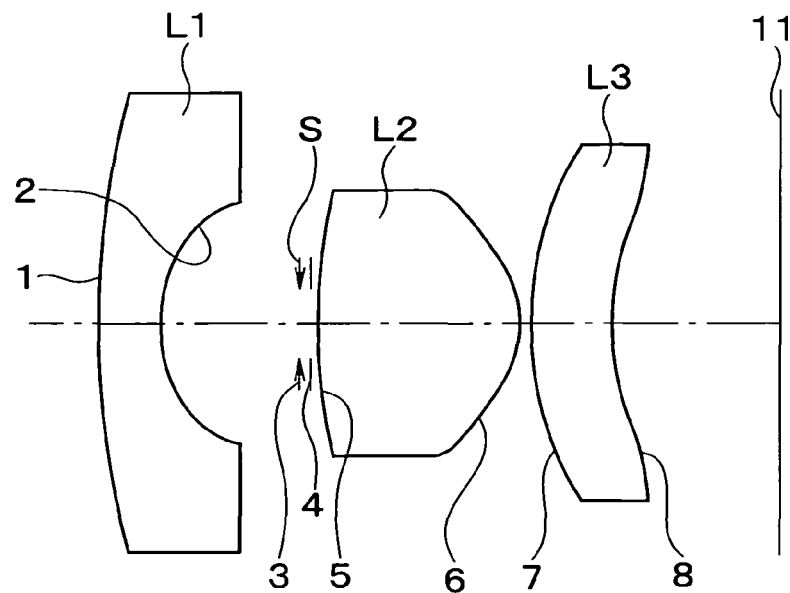
FIG. 6A is a sectional view of an objective optical system according to example 6 of the embodiment.
Figure 6B:
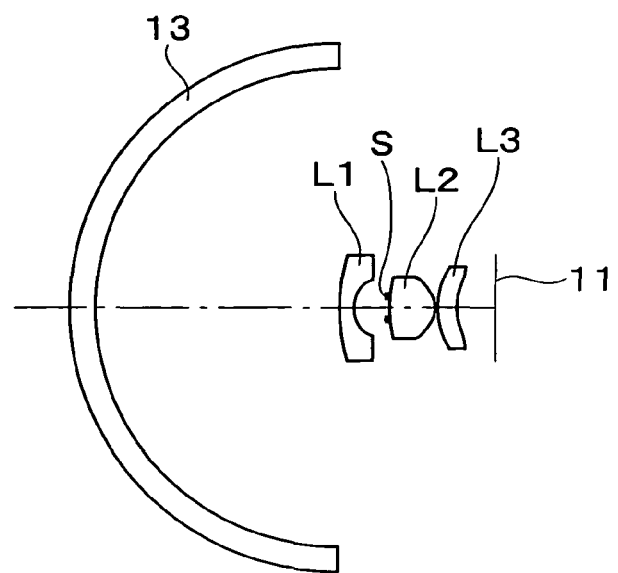
FIG. 6B is a sectional view taken when the negative-powered, dome-shaped cover is placed on an object side of the objective optical system according to example 6 of the embodiment.

FIG. 6A is a sectional view of an objective optical system according to example 6 of the present embodiment. FIG. 6B is a sectional view taken when the negative-powered, dome-shaped cover is placed on the object side of the objective optical system according to example 6 of the present embodiment. FIG. 6C is an aberration diagram of the objective optical system according to example 6 of the present embodiment. Table 6A shows numeric data on the objective optical system according to example 6 of the present embodiment. Table 6B shows numeric data obtained when the negative-powered, dome-shaped cover was placed on the object side of the objective optical system according to example 6 of the present embodiment.

TABLE 6A

| Surface No. | R | D | N | V |
|---|---|---|---|---|
| Object position | INF | 12.9792 | | |
| 1 | 5.7108 | 0.4099 | 1.5311 | 56 |
| 2(Aspheric surface) | 0.9543 | 0.8932 | | |
| 3(Lens stop) | INF | 0.0738 | | |
| 4 | INF | 0.0410 | | |
| 5 | 3.9789 | 1.2960 | 1.5311 | 56 |
| 6(Aspheric surface) | −0.6818 | 0.0814 | | |
| 7 | 2.1867 | 0.5263 | 1.5311 | 56 |
| 8(Aspheric surface) | 1.3968 | 1.0970 | | |
| Image location | INF | | | |

Aspheric surface data

| Surface No. | K | A4 | A6 | A8 | A10 |
|---|---|---|---|---|---|
| 2 | −5.6757 | 6.0331E−01 | −1.3818E+00 | 2.6447E+00 | |
| 6 | −0.4354 | 2.6069E−01 | 2.3687E−01 | 2.0363E−01 | |
| 8 | −1.1108 | −5.8591E−02 | −2.3745E−01 | 1.7967E−01 | −3.2030E−02 |

| | |
|---|---|
| Focal length of entire system | 1.0000 |
| Focal length of first lens | −2.2147 |
| Focal length of second lens | 1.2081 |
| Focal length of third lens | −9.4372 |
| Effective f-No. | 3.4924 |
| Center magnification | −0.07329 |
| Front focus position | 0.6644 |
| Rear focus position | −0.0160 |
| Maximum image height | 1.0711 |
| Half view angle at maximum image height | −74.26 |
| Incident angle on image pickup device at maximum image height | −12.07 |
| d_L23/d_L12 | 0.081 |
| |f_L3/f_L2| | 7.811 |

TABLE 6B

| Surface No. | R | D | N | V |
|---|---|---|---|---|
| Object position | INF | 6.4213 | | |
| Object-side surface of dome | 7.3776 | 0.6831 | 1.585 | 30 |
| Image-side surface of dome | 6.6945 | 6.5169 | | |
| Object-side surface of first lens | 5.7108 | 0.4099 | 1.5311 | 56 |

| | |
|---|---|
| Focal length of entire system | 0.9975 |
| Focal length of dome | −194.929 |
| Effective f-No. | 3.4940 |
| Center magnification | −0.06983 |
| Front focus position | 7.8632 |
| Rear focus position | −0.0109 |
| Half view angle at maximum image height | −74.35 |
| Incident angle on image pickup device at maximum image height | −12.07 |
| |f_d/f| | 194.929 |

Example 7

Figure 7A:
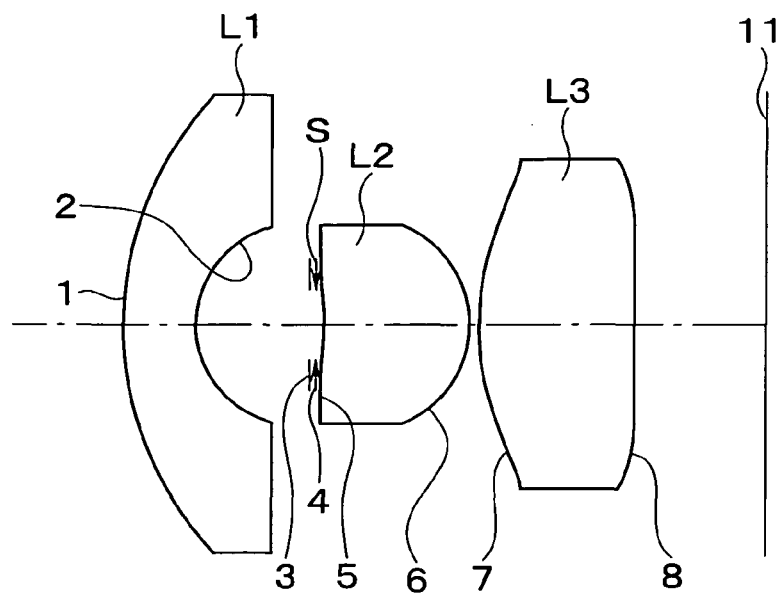
FIG. 7A is a sectional view of an objective optical system according to example 7 of the embodiment.
Figure 7B:
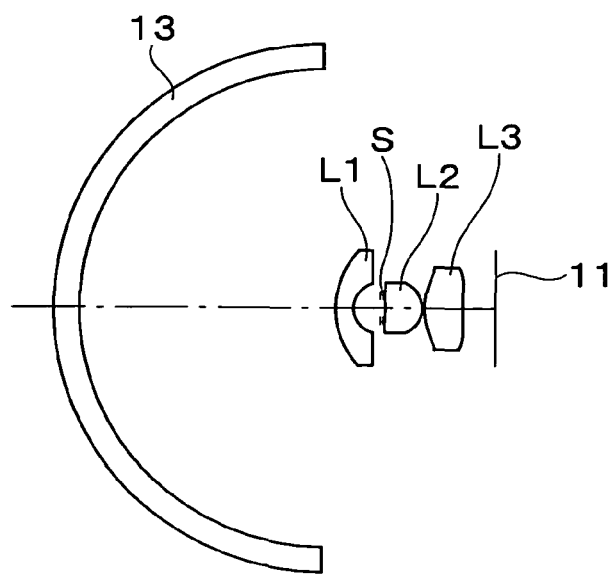
FIG. 7B is a sectional view taken when the negative-powered, dome-shaped cover is placed on an object side of the objective optical system according to example 7 of the embodiment.

FIG. 7A is a sectional view of an objective optical system according to example 7 of the present embodiment. FIG. 7B is a sectional view taken when the negative-powered, dome-shaped cover is placed on the object side of the objective optical system according to example 7 of the present embodiment. FIG. 7C is an aberration diagram of the objective optical system according to example 7 of the present embodiment. Table 7A shows numeric data on the objective optical system according to example 7 of the present embodiment. Table 7B shows numeric data obtained when the negative-powered, dome-shaped cover was placed on the object side of the objective optical system according to example 7 of the present embodiment.

TABLE 7A

| Surface No. | R | D | N | V |
|---|---|---|---|---|
| Object position | INF | 18.9819 | | |
| 1(Aspheric surface) | 2.7444 | 0.5593 | 1.5311 | 56 |
| 2(Aspheric surface) | 0.7887 | 0.9081 | | |
| 3 | INF | 0.0569 | | |
| 4(Lens stop) | INF | 0.0402 | | |
| 5(Aspheric surface) | −3.8655 | 1.1172 | 1.5311 | 56 |
| 6(Aspheric surface) | −0.8132 | 0.0759 | | |
| 7(Aspheric surface) | 2.1721 | 1.2027 | 1.5311 | 56 |
| 8(Aspheric surface) | 80.6168 | 1.0281 | | |
| Image location | INF | | | |

Aspheric surface data

| Surface No. | K | A4 | A6 | A8 |
|---|---|---|---|---|
| 1 | | 7.4011E−04 | | |
| 2 | | −8.0726E−02 | −5.4748E−02 | |
| 5 | | −5.5506E−01 | 1.0502E−01 | |
| 6 | −0.1337 | 4.8698E−02 | 5.6774E−02 | 8.7166E−03 |
| 7 | | 5.2121E−03 | −2.4712E−02 | |
| 8 | 3048.7000 | 1.3836E−02 | −4.6871E−02 | 5.9748E−03 |

| | |
|---|---|
| Focal length of entire system | 1.0000 |
| Focal length of first lens | −2.3045 |
| Focal length of second lens | 1.7128 |
| Focal length of third lens | 4.1630 |
| Effective f-No. | 3.0013 |
| Center magnification | −0.05021 |

TABLE 7A-continued

| | |
|---|---|
| Front focus position | 0.9358 |
| Rear focus position | −0.0422 |
| Maximum image height | 1.2073 |
| Half view angle at maximum image height | −81.50 |
| Incident angle on image pickup device at maximum image height | −4.35 |
| d_L23/d_L12 | 0.076 |
| |f_L3/f_L2| | 2.431 |

TABLE 7B

| Surface No. | R | D | N | V |
|---|---|---|---|---|
| Object position | INF | 12.3382 | | |
| Object-side surface of dome | 8.5419 | 0.9491 | 1.585 | 30 |
| Image-side surface of dome | 7.5928 | 8.1622 | | |
| Object-side surface of first lens | 2.7444 | 0.5593 | 1.5311 | 56 |

| | |
|---|---|
| Focal length of entire system | 0.9919 |
| Focal length of dome | −184.237 |
| Effective f-No. | 3.0008 |
| Center magnification | −0.04433 |
| Front focus position | 10.0349 |
| Rear focus position | −0.0368 |
| Half view angle at maximum image height | −81.98 |
| Incident angle on image pickup device at maximum image height | −4.35 |
| |f_d/f| | 184.237 |

Example 8

Figure 8A:
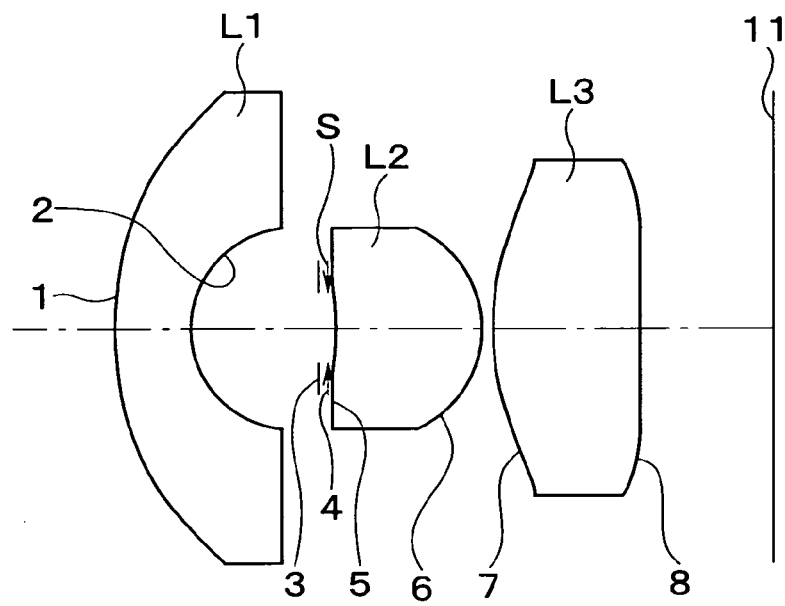
FIG. 8A is a sectional view of an objective optical system according to example 8 of the embodiment.
Figure 8B:
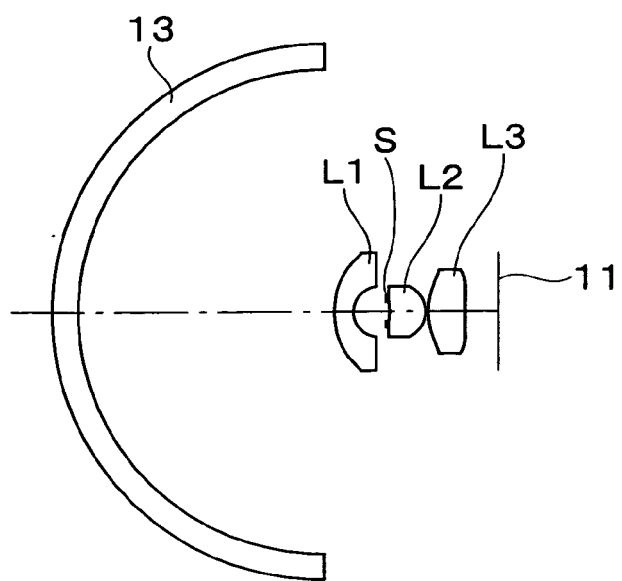
FIG. 8B is a sectional view taken when the negative-powered, dome-shaped cover is placed on an object side of the objective optical system according to example 8 of the embodiment.

FIG. 8A is a sectional view of an objective optical system according to example 8 of the present embodiment. FIG. 8B is a sectional view taken when the negative-powered, dome-shaped cover is placed on the object side of the objective optical system according to example 8 of the present embodiment. FIG. 8C is an aberration diagram of the objective optical system according to example 8 of the present embodiment. Table 8A shows numeric data on the objective optical system according to example 8 of the present embodiment. Table 8B shows numeric data obtained when the negative-powered, dome-shaped cover was placed on the object side of the objective optical system according to example 8 of the present embodiment.

TABLE 8A

| Surface No. | R | D | N | V |
|---|---|---|---|---|
| Object position | INF | 20.5324 | | |
| 1(Aspheric surface) | 4.1011 | 0.6435 | 1.5311 | 56 |
| 2(Aspheric surface) | 0.8615 | 1.1301 | | |
| 3 | INF | 0.0648 | | |
| 4(Lens stop) | INF | 0.0417 | | |
| 5(Aspheric surface) | −5.4544 | 1.2802 | 1.5311 | 56 |
| 6(Aspheric surface) | −0.9233 | 0.0865 | | |
| 7(Aspheric surface) | 2.3400 | 1.2545 | 1.5311 | 56 |
| 8(Aspheric surface) | 90.1975 | 1.1766 | | |
| Image location | INF | | | |

TABLE 8A-continued

Aspheric surface data

| Surface No. | K | A4 | A6 | A8 |
|---|---|---|---|---|
| 1 | | 3.4526E−02 | −3.0652E−03 | |
| 2 | | −1.6133E−02 | 9.9237E−02 | |
| 5 | | −3.6191E−01 | 1.1123E−02 | |
| 6 | −0.1600 | 3.4563E−02 | 6.5255E−02 | −6.1639E−02 |
| 7 | | 9.0842E−03 | −1.8233E−02 | |
| 8 | 3053.9000 | 2.5947E−02 | −3.0978E−02 | 2.5270E−03 |

| | |
|---|---|
| Focal length of entire system | 1.0000 |
| Focal length of first lens | −2.1967 |
| Focal length of second lens | 1.8975 |
| Focal length of third lens | 4.4819 |
| Effective f-No. | 3.0085 |
| Center magnification | −0.04623 |
| Front focus position | 1.0963 |
| Rear focus position | −0.0370 |
| Maximum image height | 1.3746 |
| Half view angle at maximum image height | −81.50 |
| Incident angle on image pickup device at maximum image height | −4.38 |
| d_L23/d_L12 | 0.070 |
| |f_L3/f_L2| | 2.362 |

TABLE 8B

| Surface No. | R | D | N | V |
|---|---|---|---|---|
| Object position | INF | 11.8872 | | |
| Object-side surface of dome | 9.7259 | 1.0807 | 1.585 | 30 |
| Image-side surface of dome | 8.6452 | 9.2936 | | |
| Object-side surface of first lens | 4.1011 | 0.6435 | 1.5311 | 56 |

| | |
|---|---|
| Focal length of entire system | 0.9918 |
| Focal length of dome | −209.774 |
| Effective f-No. | 3.0090 |
| Center magnification | −0.04249 |
| Front focus position | 11.4562 |
| Rear focus position | −0.0323 |
| Half view angle at maximum image height | −82.03 |
| Incident angle on image pickup device at maximum image height | −4.38 |
| |f_d/f| | 209.774 |

Example 9

Figure 9A:
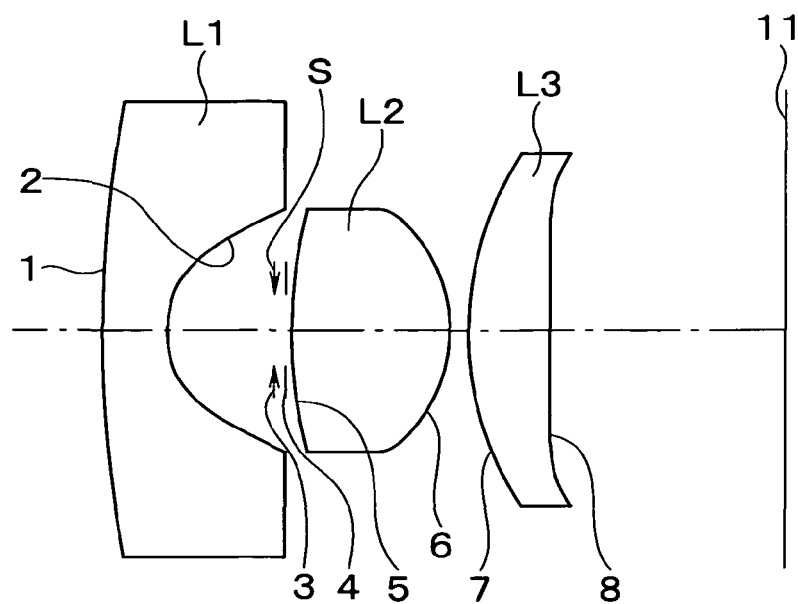
FIG. 9A is a sectional view of an objective optical system according to example 9 of the embodiment.
Figure 9B:
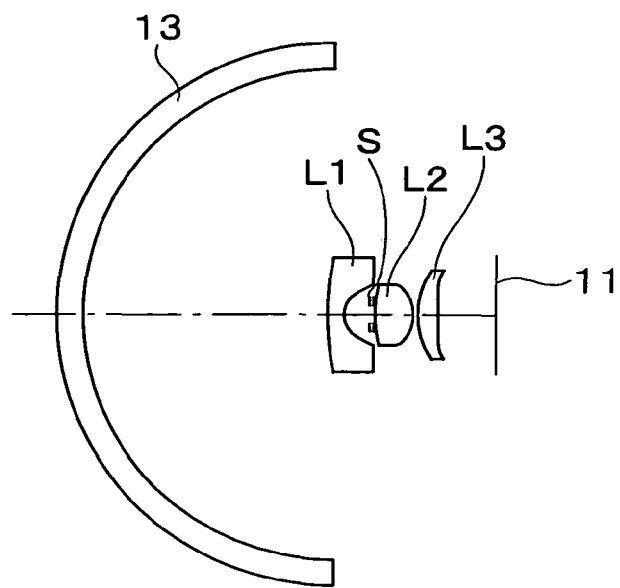
FIG. 9B is a sectional view taken when the negative-powered, dome-shaped cover is placed on an object side of the objective optical system according to example 9 of the embodiment.

FIG. 9A is a sectional view of an objective optical system according to example 9 of the present embodiment. FIG. 9B is a sectional view taken when the negative-powered, dome-shaped cover is placed on the object side of the objective optical system according to example 9 of the present embodiment. FIG. 9C is an aberration diagram of the objective optical system according to example 9 of the present embodiment. Table 9A shows numeric data on the objective optical system according to example 9 of the present embodiment. Table 9B shows numeric data obtained when the negative-powered, dome-shaped cover was placed on the object side of the objective optical system according to example 9 of the present embodiment.

TABLE 9A

| Surface No. | R | D | N | V |
|---|---|---|---|---|
| Object position | INF | 12.9904 | | |
| 1 | 8.4387 | 0.4102 | 1.5311 | 56 |
| 2(Aspheric surface) | 0.6793 | 0.7001 | | |
| 3(Lens stop) | INF | 0.0738 | | |
| 4 | INF | 0.0410 | | |
| 5 | 3.5183 | 1.0150 | 1.5311 | 56 |
| 6(Aspheric surface) | −0.9985 | 0.1311 | | |
| 7 | 2.1890 | 0.5267 | 1.5311 | 56 |
| 8(Aspheric surface) | −24.4866 | 1.5332 | | |
| Image location | INF | | | |

Aspheric surface data

| Surface No. | K | A4 | A6 | A8 |
|---|---|---|---|---|
| 2 | −1.25710 | 5.1682E−01 | 2.8141E+00 | −3.5807E+00 |
| 6 | 0.52500 | 1.6922E−01 | −5.6605E−02 | 4.1504E−01 |
| 8 | −4019.70000 | −1.9618E−02 | 9.5606E−02 | −1.3301E−02 |

| | |
|---|---|
| Focal length of entire system | 1.0000 |
| Focal length of first lens | −1.4110 |
| Focal length of second lens | 1.5819 |
| Focal length of third lens | 3.7934 |
| Effective f-No. | 3.4956 |
| Center magnification | −0.07403 |
| Front focus position | 0.5183 |
| Rear focus position | −0.0619 |
| Maximum image height | 1.0721 |
| Half view angle at maximum image height | −72.25 |
| Incident angle on image pickup device at maximum image height | −13.05 |
| d_L23/d_L12 | 0.161 |
| |f_L3/f_L2| | 2.398 |

TABLE 9B

| Surface No. | R | D | N | V |
|---|---|---|---|---|
| Object position | INF | 6.4268 | | |
| Object-side surface of dome | 7.3840 | 0.6837 | 1.585 | 30 |
| Image-side surface of dome | 6.7003 | 6.5225 | | |
| Object-side surface of first lens | 8.4387 | 0.4102 | 1.5311 | 56 |

| | |
|---|---|
| Focal length of entire system | 0.9983 |
| Focal length of dome | −195.097 |
| Effective f-No. | 3.4971 |
| Center magnification | −0.07054 |
| Front focus position | 7.7240 |
| Rear focus position | −0.0567 |
| Half view angle at maximum image height | −72.30 |
| Incident angle on image pickup device at maximum image height | −13.05 |
| |f_d/f| | 195.097 |

Example 10

Figure 10A:
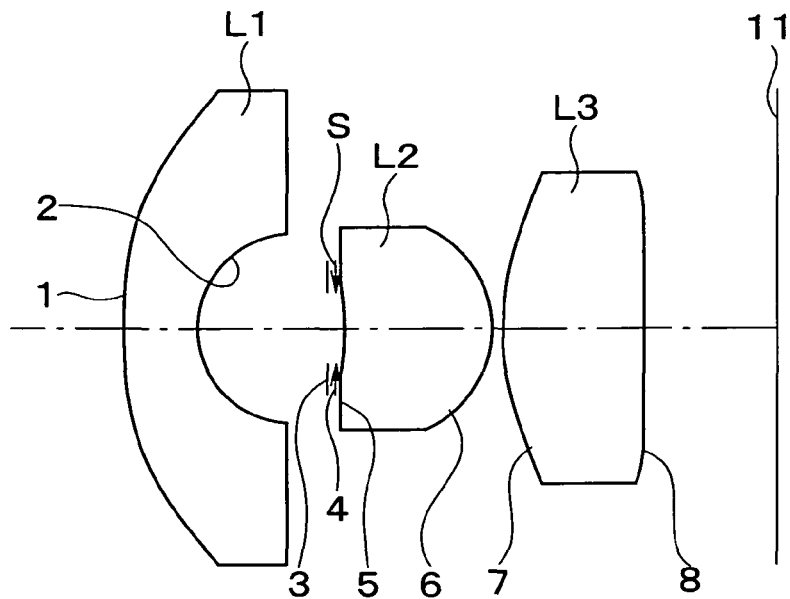
FIG. 10A is a sectional view of an objective optical system according to example 10 of the embodiment.
Figure 10B:
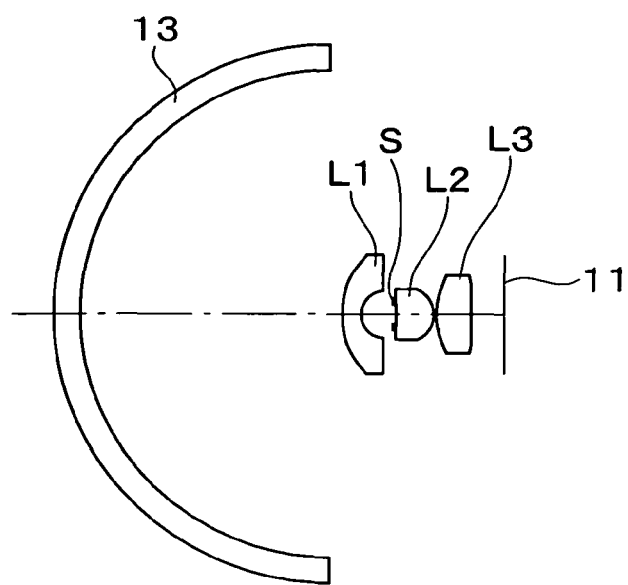
FIG. 10B is a sectional view taken when the negative-powered, dome-shaped cover is placed on an object side of the objective optical system according to example 10 of the embodiment.

FIG. 10A is a sectional view of an objective optical system according to example 10 of the present embodiment. FIG. 10B is a sectional view taken when the negative-powered, dome-shaped cover is placed on the object side of the objective optical system according to example 10 of the present embodiment. FIG. 10C is an aberration diagram of the objective optical system according to the present embodiment. Table 10A shows numeric data on the objective optical system according to example 10 of the present embodiment. Table 10B shows numeric data obtained when the negative-powered, dome-shaped cover was placed on the object side of the objective optical system according to example 10 of the present embodiment.

TABLE 10A

| Surface No. | R | D | N | V |
|---|---|---|---|---|
| Object position | INF | 21.9613 | | |
| 1(Aspheric surface) | 7.2240 | 0.6846 | 1.5311 | 56 |
| 2(Aspheric surface) | 0.9216 | 1.2442 | | |
| 3 | INF | 0.0694 | | |
| 4(Lens stop) | INF | 0.0381 | | |
| 5(Aspheric surface) | −10.8548 | 1.3833 | 1.5311 | 56 |
| 6(Aspheric surface) | −0.9916 | 0.0925 | | |
| 7(Aspheric surface) | 2.6101 | 1.3172 | 1.5311 | 56 |
| 8(Aspheric surface) | 90.2364 | 1.2483 | | |
| Image location | INF | | | |

Aspheric surface data

| Surface No. | K | A4 | A6 | A8 |
|---|---|---|---|---|
| 1 | | 4.4114E−02 | −6.4927E−03 | 3.0168E−04 |
| 2 | | 2.0608E−02 | 1.2721E−01 | |
| 5 | | −2.7632E−01 | −6.7702E−02 | |
| 6 | −0.2416 | 2.2531E−02 | 3.6072E−02 | −4.8467E−02 |
| 7 | | 9.8881E−03 | −2.2333E−02 | 4.2332E−03 |
| 8 | 2986.3000 | 2.6016E−02 | −2.7430E−02 | 3.7796E−03 |

| | |
|---|---|
| Focal length of entire system | 1.0000 |
| Focal length of first lens | −2.0585 |
| Focal length of second lens | 1.9510 |
| Focal length of third lens | 5.0133 |
| Effective f-No. | 2.9809 |
| Center magnification | −0.04332 |
| Front focus position | 1.1205 |
| Rear focus position | −0.0335 |
| Maximum image height | 1.4703 |
| Half view angle at maximum image height | −81.52 |
| Incident angle on image pickup device at maximum image height | −8.73 |
| d_L23/d_L12 | 0.068 |
| \|f_L3/f_L2\| | 2.570 |

TABLE 10B

| Surface No. | R | D | N | V |
|---|---|---|---|---|
| Object position | INF | 13.8703 | | |
| Object-side surface of dome | 10.4027 | 1.1559 | 1.585 | 30 |
| Image-side surface of dome | 9.2469 | 9.9404 | | |
| Object-side surface of first lens | 7.2240 | 0.6846 | 1.5311 | 56 |

| | |
|---|---|
| Focal length of entire system | 0.9920 |
| Focal length of dome | −224.373 |
| Effective f-No. | 2.9804 |
| Center magnification | −0.03805 |
| Front focus position | 12.2022 |
| Rear focus position | −0.0291 |
| Half view angle at maximum image height | −82.00 |
| Incident angle on image pickup device at maximum image height | −8.73 |
| \|f_d/f\| | 224.373 |

Example 11

Figure 11A:
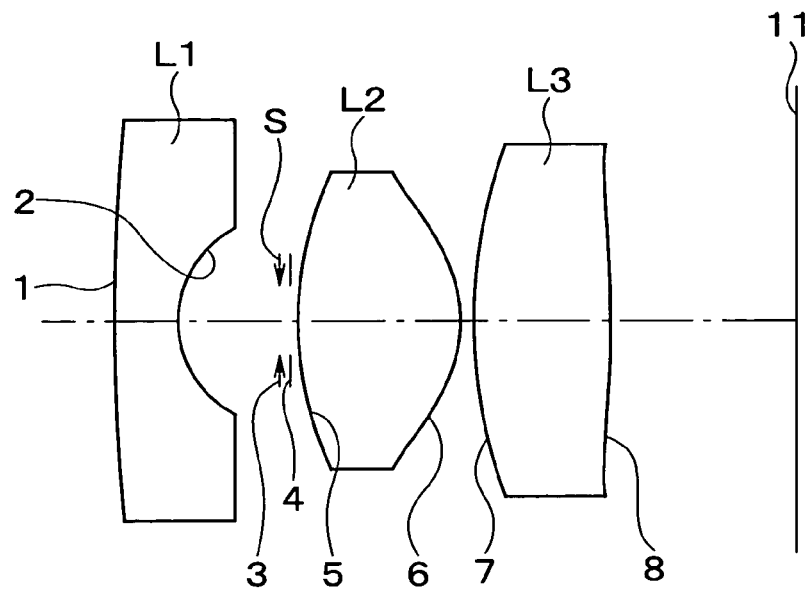
FIG. 11A is a sectional view of an objective optical system according to example 11 of the embodiment.
Figure 11B:
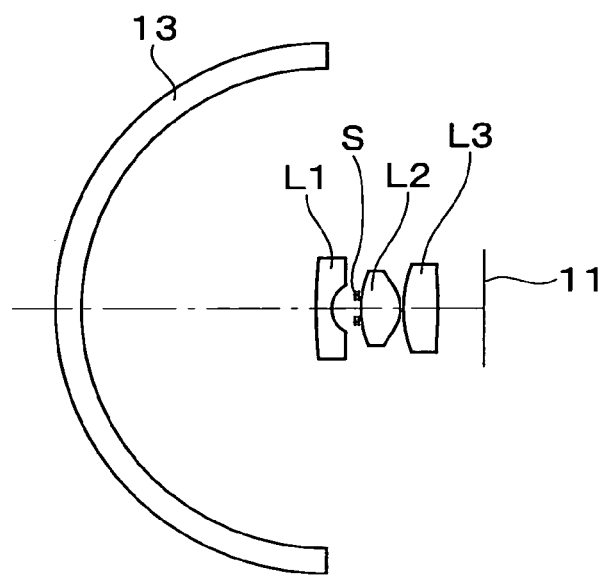
FIG. 11B is a sectional view taken when the negative-powered, dome-shaped cover is placed on an object side of the objective optical system according to example 11 of the embodiment.
Figure 11C:
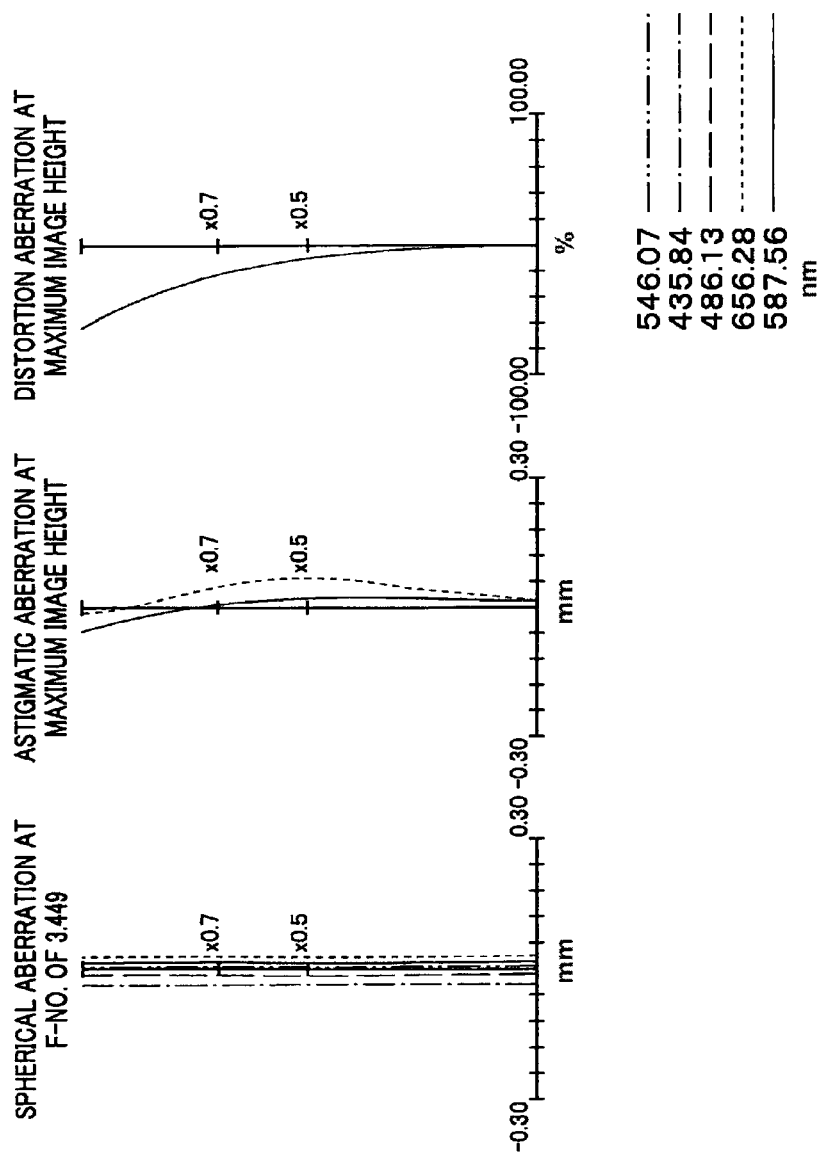
FIG. 11C is an aberration diagram of the objective optical system according to example 11 of the embodiment.

FIG. 11A is a sectional view of an objective optical system according to example 11 of the present embodiment. FIG. 11B is a sectional view taken when the negative-powered, dome-shaped cover is placed on the object side of the objective optical system according to example 11 of the present embodiment. FIG. 11C is an aberration diagram of the objective optical system according to example 11 of the present embodiment. Table 11A shows numeric data on the objective optical system according to example 11 of the present embodiment. Table 11B shows numeric data obtained when the negative-powered, dome-shaped cover was placed on the object side of the objective optical system according to example 11 of the present embodiment.

TABLE 11A

| Surface No. | R | D | N | V |
|---|---|---|---|---|
| Object position | | 15.4515 | | |
| 1 | 17.8334 | 0.4102 | 1.5311 | 56 |
| 2(Aspheric surface) | 0.7316 | 0.6563 | | |
| 3(Lens stop) | INF | 0.0738 | | |
| 4 | INF | 0.0410 | | |
| 5 | 2.4613 | 1.0529 | 1.5311 | 56 |
| 6(Aspheric surface) | −0.9120 | 0.0820 | | |
| 7 | 3.3351 | 0.9025 | 1.5311 | 56 |
| 8(Aspheric surface) | 12.6223 | 1.2170 | | |
| Image location | INF | | | |

Aspheric surface data

| Surface No. | K | A4 | A6 | A8 |
|---|---|---|---|---|
| 2 | 0.2982 | −1.4239E−01 | −1.2448E−01 | −3.2467E−01 |
| 6 | −1.4564 | −1.5383E−02 | −4.5510E−02 | 1.0126E−01 |
| 8 | 9.8211 | −1.9741E−02 | 1.8430E−03 | 1.5057E−02 |

| | |
|---|---|
| Focal length of entire system | 1.0000 |
| Focal length of first lens | −1.4423 |
| Focal length of second lens | 1.3996 |
| Focal length of third lens | 5.0453 |
| Effective f-No. | 3.5003 |
| Center magnification | −0.06272 |
| Front focus position | 0.4922 |
| Rear focus position | −0.0565 |
| Maximum image height | 1.0720 |
| Half view angle at maximum image height | −71.67 |
| Incident angle on image pickup device at maximum image height | −13.14 |
| d_L23/d_L12 | 0.106 |
| \|f_L3/f_L2\| | 3.605 |

TABLE 11B

| Surface No. | R | D | N | V |
|---|---|---|---|---|
| Object position | | 9.7084 | | |
| Object-side surface of dome | 7.3839 | 0.6837 | 1.585 | 30 |
| Image-side surface of dome | 6.7002 | 6.5224 | | |
| Object-side surface of first lens | 17.8334 | 0.4102 | 1.5311 | 56 |

| | |
|---|---|
| Focal length of entire system | 0.9984 |
| Focal length of dome | −195.094 |
| Effective f-No. | 3.4999 |
| Center magnification | −0.05736 |
| Front focus position | 7.6978 |

TABLE 11B-continued

| | |
|---|---|
| Rear focus position | −0.0514 |
| Half view angle at maximum image height | −71.71 |
| Incident angle on image pickup device at maximum image height | −13.14 |
| \|f_d/f\| | 195.094 |

Example 12

Figure 12A:
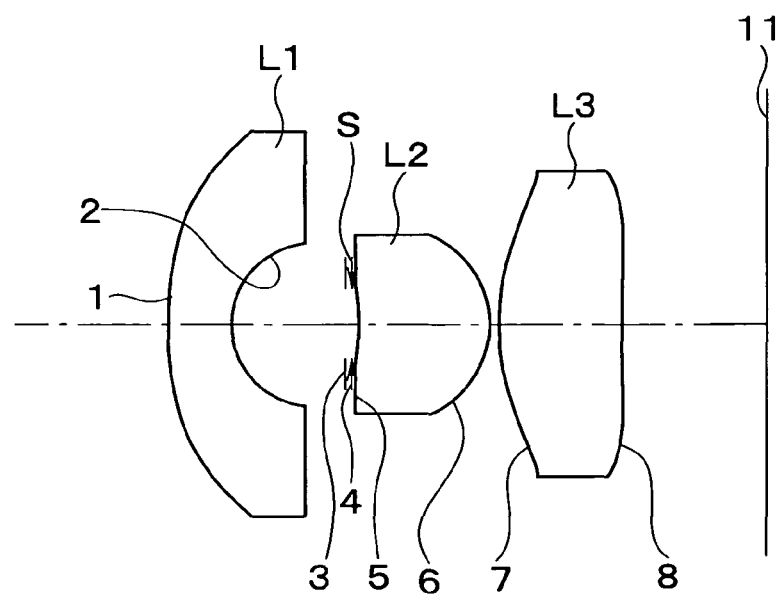
FIG. 12A is a sectional view of an objective optical system according to example 12 of the embodiment.
Figure 12B:
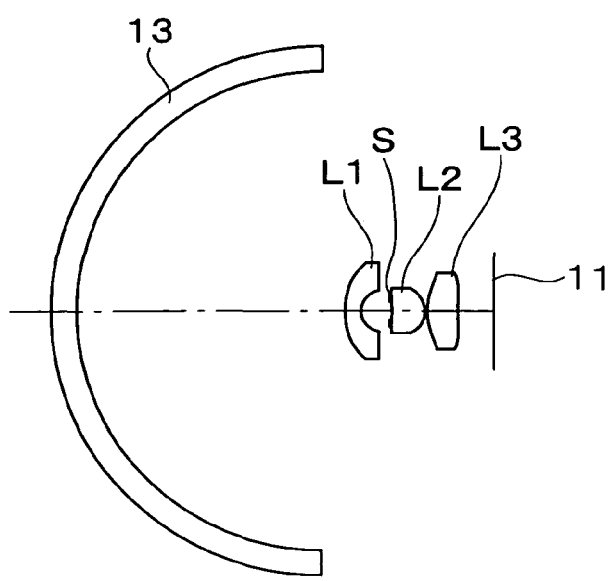
FIG. 12B is a sectional view taken when the negative-powered, dome-shaped cover is placed on an object side of the objective optical system according to example 12 of the embodiment.

FIG. 12A is a sectional view of an objective optical system according to example 12 of the present embodiment. FIG. 12B is a sectional view taken when the negative-powered, dome-shaped cover is placed on the object side of the objective optical system according to example 12 of the present embodiment. FIG. 12C is an aberration diagram of the objective optical system according to example 12 of the present embodiment. Table 12A shows numeric data on the objective optical system according to example 12 of the present embodiment. Table 12B shows numeric data obtained when the negative-powered, dome-shaped cover was placed on the object side of the objective optical system according to example 12 of the present embodiment.

TABLE 12A

| Surface No. | R | D | N | V |
|---|---|---|---|---|
| Object position | | 18.7899 | | |
| 1(Aspheric surface) | 3.7531 | 0.5889 | 1.5311 | 56 |
| 2(Aspheric surface) | 0.7884 | 1.0342 | | |
| 3 | INF | 0.0593 | | |
| 4(Lens stop) | INF | 0.0382 | | |
| 5(Aspheric surface) | −4.9915 | 1.1716 | 1.45 | 50 |
| 6(Aspheric surface) | −0.8450 | 0.0791 | | |
| 7(Aspheric surface) | 2.1414 | 1.1481 | 1.6 | 20 |
| 8(Aspheric surface) | 82.5429 | 1.0768 | | |
| Image location | INF | | | |

Aspheric surface data

| Surface No. | K | A4 | A6 | A8 |
|---|---|---|---|---|
| 1 | | 4.5050E−02 | −4.7756E−03 | |
| 2 | | −2.1051E−02 | 1.5461E−01 | |
| 5 | | −4.7222E−01 | 1.7329E−02 | |
| 6 | −0.16002 | 4.51E−02 | 1.02E−01 | −1.15E−01 |
| 7 | | 1.19E−02 | −2.84E−02 | 0.00E+00 |
| 8 | 3053.9 | 3.39E−02 | −4.45E−02 | 4.16E−03 |

| | |
|---|---|
| Focal length of entire system | 1.0000 |
| Focal length of first lens | −2.0102 |
| Focal length of second lens | 2.0678 |
| Focal length of third lens | 3.6026 |
| Effective f-No. | 3.2873 |
| Center magnification | −0.04427 |
| Front focus position | 0.9778 |
| Rear focus position | −0.0440 |
| Maximum image height | 1.2579 |
| Half view angle at maximum image height | −74.33 |

TABLE 12A-continued

| | |
|---|---|
| Incident angle on image pickup device at maximum image height | −3.74 |
| d_L23/d_L12 | 0.070 |
| \|f_L3/f_L2\| | 1.742 |

TABLE 12B

| Surface No. | R | D | N | V |
|---|---|---|---|---|
| Object position | | 12.9678 | | |
| Object-side surface of dome | 9.7259 | 1.0807 | 1.585 | 30 |
| Image-side surface of dome | 8.6452 | 9.2936 | | |
| Object-side surface of first lens | 3.7531 | 0.5889 | 1.5311 | 56 |

| | |
|---|---|
| Focal length of entire system | 0.9923 |
| Focal length of dome | −209.774 |
| Effective f-No. | 3.4999 |
| Center magnification | −0.04082 |
| Front focus position | 11.3396 |
| Rear focus position | −0.0393 |
| Half view angle at maximum image height | −74.83 |
| Incident angle on image pickup device at maximum image height | −13.14 |
| \|f_d/f\| | 209.774 |

Example 13

Figure 13A:
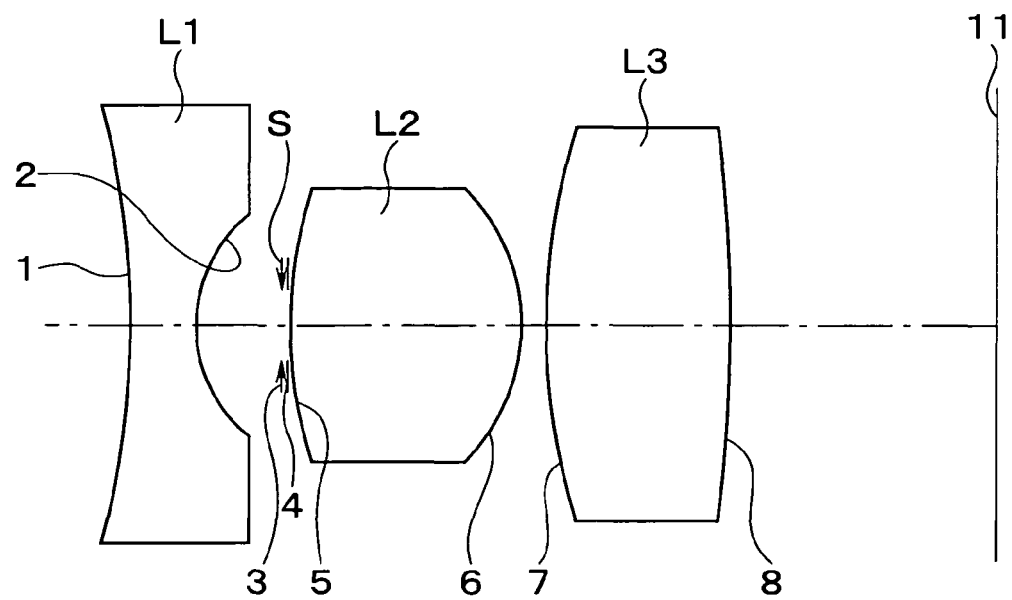
FIG. 13A is a sectional view of an objective optical system according to example 13 of the embodiment.
Figure 13B:
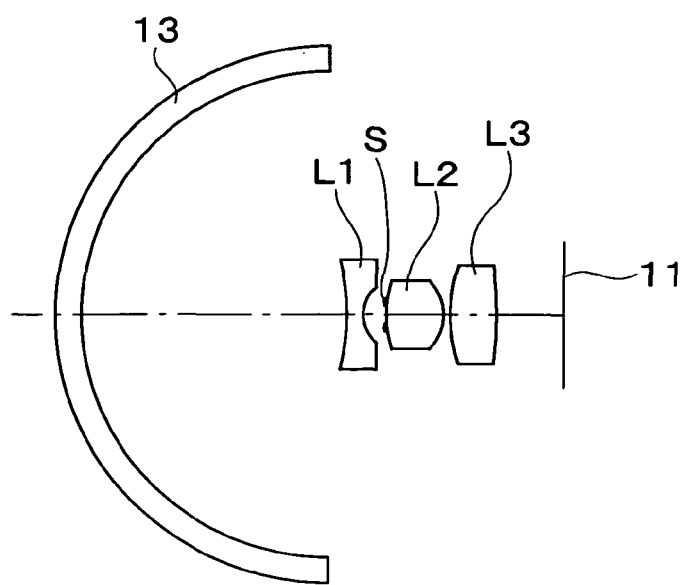
FIG. 13B is a sectional view taken when the negative-powered, dome-shaped cover is placed on an object side of the objective optical system according to example 13 of the embodiment.

FIG. 13A is a sectional view of an objective optical system according to example 13 of the present embodiment. FIG. 13B is a sectional view taken when the negative-powered, dome-shaped cover is placed on the object side of the objective optical system according to example 13 of the present embodiment. FIG. 13C is an aberration diagram of the objective optical system according to example 13 of the present embodiment. Table 13A shows numeric data on the objective optical system according to example 13 of the present embodiment. Table 13B shows numeric data obtained when the negative-powered, dome-shaped cover was placed on the object side of the objective optical system according to example 13 of the present embodiment.

TABLE 13A

| Surface No. | R | D | N | V |
|---|---|---|---|---|
| Object position | | 10.6302 | | |
| 1 | −4.6427 | 0.3189 | 1.52985 | 56 |
| 2 | 0.6935 | 0.4020 | | |
| 3 (Lens stop) | INF | 0.0213 | | |

TABLE 13A-continued

| | | | | |
|---|---|---|---|---|
| 4 | INF | 0.0116 | | |
| 5 | 2.1349 | 1.1101 | 1.52985 | 56 |
| 6(Aspheric surface) | −0.8111 | 0.1071 | | |
| 7 | 3.2118 | 0.8750 | 1.52985 | 56 |
| 8(Aspheric surface) | −9.2352 | 1.2728 | | |
| Image location | INF | | | |

Aspheric surface data

| Surface No. | K | A4 | A6 | A8 | A10 |
|---|---|---|---|---|---|
| 6 | −1.0888 | −7.8682E−02 | −2.2607E−01 | 6.4449E−01 | −1.73E−01 |
| 8 | −1.17E−05 | −1.7809E−02 | 3.0814E−02 | −2.2010E−02 | −7.16E−05 |

| | |
|---|---|
| Focal length of entire system | 1.0000 |
| Focal length of first lens | −1.1108 |
| Focal length of second lens | 1.2710 |
| Focal length of third lens | 4.5906 |
| Effective f-No. | 3.3894 |
| Center magnification | −0.09178 |
| Front focus position | 0.2651 |
| Rear focus position | −0.0607 |
| Maximum image height | 0.9326 |
| Half view angle at maximum image height | −69.06 |
| Incident angle on image pickup device at maximum image height | −11.18 |
| d_L23/d_L12 | 0.246 |
| \|f_L3/f_L2\| | 3.612 |

TABLE 13B

| Surface No. | R | D | N | V |
|---|---|---|---|---|
| Object position | | 10.6302 | | |
| Object-side surface of dome | 5.3531 | 0.5948 | 1.585 | 30 |
| Image-side surface of dome | 4.7583 | 5.1152 | | |
| Object-side surface of first lens | −4.6427 | 0.3189 | 1.52985 | 56 |

| | |
|---|---|
| Focal length of entire system | 0.9946 |
| Focal length of dome | −115.458 |
| Effective f-No. | 3.4999 |
| Center magnification | −0.04082 |
| Front focus position | 5.9717 |
| Rear focus position | −0.0520 |
| Half view angle at maximum image height | −69.31 |
| Incident angle on image pickup device at maximum image height | −11.18 |
| \|f_d/f\| | 115.458 |

Among the examples described above, the groups of the objective optical systems in examples 1 to 11 and 13 are all made of the same resin material. This eliminates the need for processes and the like required when different resin materials are used, such as a manufacturing equipment cleaning process needed when resins are changed or a setup needed when manufacturing conditions are changed, and thereby realizes a still lower-cost objective optical system.

On the other hand, in example 12, the lens of the third group is made of a material with a lower Abbe number than the lens of the second group to correct chromatic difference of magnification.

Thus, according to the present embodiment, all the lenses can be made of a material with a refractive index of 1.65 or less. Typical materials with a refractive index of 1.65 or less include resin materials such as cycloolefin polymer, polycarbonate, acrylic, and polysulfone. The lenses can be manufactured from the resin materials at lower cost than from glass. Consequently, a wide-angle objective optical system with wide angle of view of 130 degrees or more can be manufactured at low cost.

Also, in an apparatus such as an endoscope or a capsule endoscope which is inserted into the body for observation, as shown in FIGS. 1B to 13B, the endoscopic objective optical system is configured by placing the dome-shaped, transparent cover 13 on the object side of the objective optical system (on a distal end side of the apparatus) in an attempt to minimize friction with the body interior and thereby reduce the burden on the patient. Such a structure has a problem in that the beam is refracted by the dome-shaped cover 13, changing the angle of incidence on the objective optical system and resulting in changes in optical performance and imaging performance from when no cover 13 is used.

Thus, in the present embodiment, the absolute value of the focal length of the dome-shaped cover 13 is set to be sufficiently larger than the absolute value of the focal length of the objective optical system, i.e., the following conditional expression is satisfied.

$$100 < |f\_d/f|$$

where f_d is the focal length of the dome-shaped cover 13 and f is the focal length of the entire objective optical system when the cover 13 is not placed.

In examples 1 to 13 described above, as can be seen from Tables 1A to 13A and Tables 1B to 13B, the absolute value of the focal length of the dome-shaped cover 13 is sufficiently larger than the absolute value of the focal length of the objective optical system (over 100 times as shown by the aforementioned conditional expression), and thus the dome-shaped cover 13 has a minimal effect with respect to power on the entire endoscopic objective optical system including the cover 13 and the objective optical system. Consequently, there is substantially no difference in observation performance whether or not the cover 13 is placed.

Also, in the examples described above, sphere center positions on the object-side and image-side surfaces of the dome-shaped cover 13 are made to coincide with each other. Consequently, the beams passing through sphere centers are not refracted. This further reduces changes in the optical performance caused by the cover 13.

Figure 14:
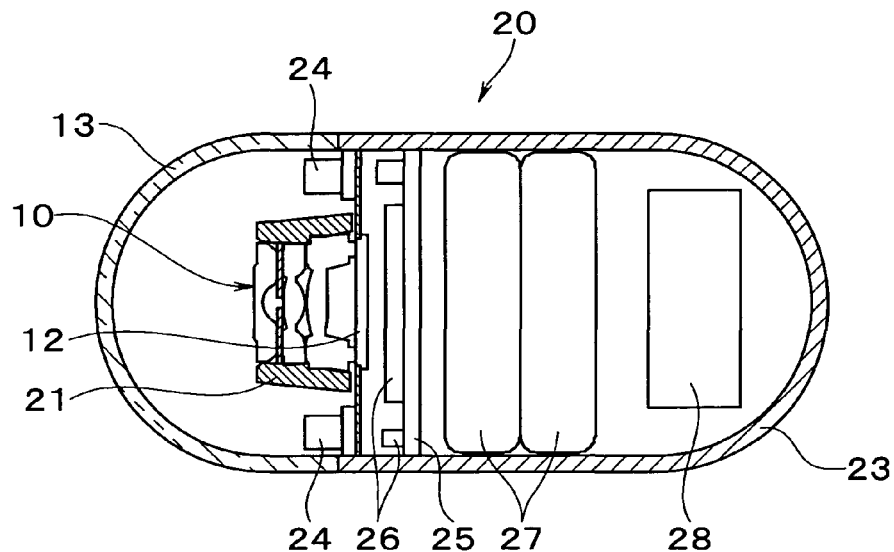
FIG. 14 is a diagram showing a schematic configuration of principal part of a capsule endoscope equipped with the objective optical system according to the embodiment.

FIG. 14 is a diagram showing a schematic configuration of principal part of a capsule endoscope 20 equipped with the objective optical system according to the present embodiment.

The objective optical system 10 according to the present embodiment is housed in an objective frame 21. Also, the image pickup surface 11 of the image pickup device 12 is placed to coincide with the image plane position of the objective optical system 10. The image pickup device 12 has its position located by being abutted against part of the objective optical system 10.

Illumination members such as LEDs 24 are placed around the objective optical system 10 and the image pickup device 12 to illuminate an object whose image is to be picked up. In the example shown in FIG. 14, to provide illumination which does not produce shades on the object, a plurality (e.g., two) of LEDs 24 are placed at substantially symmetrical positions with respect to the objective optical system 10.

The objective optical system 10, the image pickup device 12, and the LEDs 24 are placed on the object side of an exterior part 23 which makes up an enclosure of the capsule endoscope 20. The dome-shaped (e.g., substantially hemispherical) cover 13 made of a transparent material is placed, extending from the object side of the exterior part 23 to cover the objective optical system 10, the image pickup device 12, and the LEDs 24. The dome-shaped cover 13 has negative power on the optical axis of the objective optical system 10 as shown in Tables 1B to 13B.

Also, the exterior part 23 houses a substrate 25, a battery 27, and a radio apparatus 28, where electrical components 26 used to drive the image pickup device 12 and the LEDs 24 or to process images obtained by the image pickup device 12 are mounted on the substrate 25, the battery 27 is configured to serve as a power supply for the capsule endoscope 20, and the radio apparatus 28 is configured to transmit the obtained images to the outside and receive commands from the outside.

In the configuration shown in FIG. 14, it is assumed that the LEDs 24 emit light only in the visible range and an amount of infrared radiation is assumed to be almost zero. Also, it is assumed that an operating environment of the capsule endoscope 20 is in a body cavity. Consequently, since the capsule endoscope 20 is almost unaffected by extraneous light or the like, there is no need to consider infrared radiation of any extraneous light. Therefore, there is no need to provide a filter or coating configured to cut infrared radiation, in the endoscopic objective optical system including the cover 13 and the objective optical system 10. This makes it possible to obtain a still lower-cost objective optical system.

Figure 15:
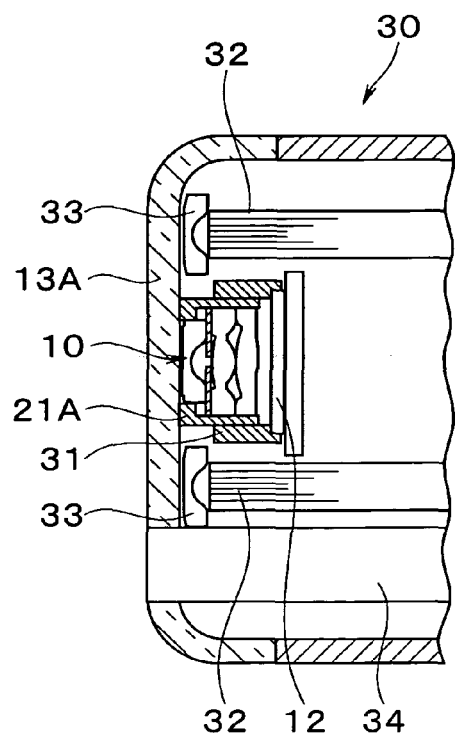
FIG. 15 is a diagram showing a schematic configuration of a distal end portion of an endoscope equipped with the objective optical system according to the embodiment.

FIG. 15 is a diagram showing a schematic configuration of a distal end portion 30 of an endoscope equipped with the objective optical system 10 according to the present embodiment.

The objective optical system 10 according to the present embodiment is housed in an objective frame 21A. Also, the image pickup device 12 is held by an image pickup device frame 31. An outer circumference of the objective frame 21A is fitted in an inner circumference of the image pickup device frame 31 slidably along the optical axis. The image pickup device 12 and the objective optical system 10 are designed to have their positions located as the objective frame 21A and the image pickup device frame 31 are adjusted by sliding. The adjustment allows the image pickup surface 11 of the image pickup device 12 to be placed accurately at the image plane position of the objective optical system 10.

Illumination lenses 33 which are illumination members configured to illuminate an object whose image is to be picked up are placed around the objective optical system 10. Light guides 32 configured to guide light from a light source device (not shown) to the illumination lenses 33 are placed behind the illumination lenses 33. Again, in the example shown in FIG. 15, to provide illumination which does not produce shades on the object, a plurality (e.g., two) of illumination lenses 33 and light guides 32 are placed at substantially symmetrical positions with respect to the objective optical system 10.

Also, a transparent cover 13A is placed to cover the object side of the objective optical system 10 and the illumination lenses 33. The cover 13A creates a watertight and airtight seal in the endoscope except for inner part of a forceps hole 34 (described later). Unlike the cover 13 of the capsule endoscope 20 described above, the cover 13A is a flat-shaped one which does not have power on the optical axis of the objective optical system 10 (and on optical axes of the illumination lenses 33).

Also, the forceps hole 34 is provided running from the distal end portion 30 of the endoscope to the user's hand side of the endoscope. The forceps hole 34 is configured to pass forceps and the like used for treatments and biopsies and is communicated to the outside by penetrating the cover 13A.

Incidentally, light containing infrared radiation could be emitted depending on the type of light source used in the light source device, and thus in the configuration shown in FIG. 15, a surface of the third group which is closest to the image side (on the side of the image pickup device 12) is coated to cut infrared radiation.

In this way, since the cover 13A is placed so as to cover the objective optical system 10, the illumination lenses 33, and the like at least on the object side, the lenses and the like of optical systems are not exposed to the outside, and thus to body fluids or the like. This allows lenses to be manufactured using a material, such as resin, which is inferior in durability to glass. Since resin materials are available relatively inexpensively, costs of the objective optical system 10, the illumination lenses 33, and the like can be reduced further.

The objective optical system according to the present embodiment is suitable for small apparatus which require a wide observation field of view. Concrete application examples include endoscopes and capsule endoscopes. Furthermore, among such apparatus, the objective optical system according to the present embodiment is useful, especially for disposable types which are desired to be low in cost.

Thus, the embodiment provides an objective optical system with a wide angle of 130 degrees or more quite serviceable for use in endoscopes at low cost while achieving downsizing by reducing the number of lenses.

It should be noted that the present invention is not limited to the precise embodiment described above and may be embodied by changing components in the implementation stage without departing from the spirit of the invention. Also, the invention can be implemented in various forms using appropriate combinations of the components disclosed in the above embodiment. For example, some of the components disclosed in the embodiment may be deleted. Furthermore, components may be combined as required across different embodiments. Thus, it is needless to say that various alterations and applications are possible without departing from the spirit of the invention.

What is claimed is:

1. An objective optical system comprising, in order from an object side, a negative-powered first group, an aperture stop, a positive-powered second group, and a third group, wherein:
   a surface of the first group which is closest to an image side is a concave surface turned toward the image side;
   a surface of the second group which is closest to the image side is an aspheric surface;
   a surface of the third group which is closest to an object side is a convex surface turned toward the object side;
   the objective optical system has a three-group, three-lens configuration in which each group is made up of a single lens, all surfaces of the three lenses have power and are configured to bend a beam by refraction, and all the three lenses of the first to third groups are optical devices made of a material with a refractive index of 1.65 or less; and
   a distance between the second group and the third group is smaller than a distance between the first group and the second group, the objective optical system satisfying a conditional expression below and having an angle of view of 130 degrees or more $d\_L23/d\_L12 < 0.25$ $1.7 < f\_L3/f\_L2$ where
d_L23 is the distance between the second group and the third group,
d_L12 is the distance between the first group and the second group,
f_L2 is a focal length of the second group, and
f_L3 is a focal length of the third group.

2. An endoscopic objective optical system comprising:
   the objective optical system according to claim 1; and
   a cover placed closer to the object side than a surface of the first group which is the closest to the object side.

3. The endoscopic objective optical system according to claim 2, wherein the cover is shaped like a dome, has negative power on an optical axis of the objective optical system, and satisfies a conditional expression below $100 < |f\_d/f|$ where
f_d is a focal length of the cover, and
f is a focal length of the entire objective optical system when the cover is not placed.

4. The endoscopic objective optical system according to claim 2, further comprising an illumination member placed around the objective optical system, wherein
   the cover is a flat-shaped one which does not have power on the optical axis of the objective optical system and is placed so as to cover the objective optical system and the illumination member.

5. The objective optical system according to claim 1, wherein all the three lenses of the first to third groups are optical devices made of a same material.

6. The objective optical system according to claim 1, wherein the objective optical system further satisfies a conditional expression below $0.052 \leq d\_L23/d\_L12$.

7. The objective optical system according to claim 1, wherein the objective optical system further satisfies a conditional expression below $2.362 \leq |f\_L3/f\_L2|$.

8. The objective optical system according to claim 1, wherein the objective optical system further satisfies a conditional expression below $2.362 \leq |f\_L3/f\_L2| \leq 3.612$.

9. An objective optical system comprising, in order from an object side, a negative-powered first group, an aperture stop, a positive-powered second group, and a third group, wherein:
   a surface of the first group which is closest to an image side is a concave surface turned toward the image side;
   a surface of the second group which is closest to the image side is an aspheric surface;
   a surface of the third group which is closest to an object side is a convex surface turned toward the object side;
   the objective optical system has a three-group, three-lens configuration in which each group is made up of a single lens, all surfaces of the three lenses have power and are configured to bend a beam by refraction, and all the three lenses of the first to third groups are optical devices made of a same material; and
   a distance between the second group and the third group is smaller than a distance between the first group and the second group, the objective optical system satisfying a conditional expression below and having an angle of view of 130 degrees or more $d\_L23/d\_L12 < 0.25$ $1.7 < f\_L3/f\_L2$ where
d_L23 is the distance between the second group and the third group,
d_L12 is the distance between the first group and the second group,
f_L2 is a focal length of the second group, and
f_L3 is a focal length of the third group.

10. An endoscopic objective optical system comprising:
    the objective optical system according to claim 9; and
    a cover placed closer to the object side than a surface of the first group which is the closest to the object side.

11. The endoscopic objective optical system according to claim 10, wherein the cover is shaped like a dome, has negative power on an optical axis of the objective optical system, and satisfies a conditional expression below $100 < |f\_d/f|$ where
f_d is a focal length of the cover, and
f is a focal length of the entire objective optical system when the cover is not placed.

12. The endoscopic objective optical system according to claim 10, further comprising an illumination member placed around the objective optical system, wherein
    the cover is a flat-shaped one which does not have power on the optical axis of the objective optical system and is placed so as to cover the objective optical system and the illumination member.

13. The objective optical system according to claim 9, wherein the objective optical system further satisfies a conditional expression below $0.052 \leq d\_L23/d\_L12$.

14. The objective optical system according to claim 9, wherein the objective optical system further satisfies a conditional expression below $2.362 \leq |f\_L3/f\_L2|$.

15. The objective optical system according to claim 9, wherein the objective optical system further satisfies a conditional expression below $$2.362 \leq |f\_L3/f\_L2| \leq 3.612.$$

* * * * *